(12) United States Patent
Talbert et al.

(10) Patent No.: US 11,716,533 B2
(45) Date of Patent: Aug. 1, 2023

(54) IMAGE SYNCHRONIZATION WITHOUT INPUT CLOCK AND DATA TRANSMISSION CLOCK IN A PULSED FLUORESCENCE IMAGING SYSTEM

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International, Zug (CH)

( * ) Notice: Subject to any disclaimer, the term of this patent is extended or adjusted under 35 U.S.C. 154(b) by 568 days.

(21) Appl. No.: 16/748,537

(22) Filed: Jan. 21, 2020

(65) Prior Publication Data

US 2020/0404169 A1 Dec. 24, 2020

Related U.S. Application Data

(60) Provisional application No. 62/864,227, filed on Jun. 20, 2019.

(51) Int. Cl.
*H04N 23/60* (2023.01)
*G01N 21/64* (2006.01)
(Continued)

(52) U.S. Cl.
CPC ....... *H04N 23/665* (2023.01); *A61B 1/00006* (2013.01); *A61B 1/043* (2013.01);
(Continued)

(58) Field of Classification Search
CPC .. H04N 5/23227; H04N 5/2256; H04N 5/378; H04N 13/239; H04N 5/332;
(Continued)

(56) References Cited

U.S. PATENT DOCUMENTS 5,318,024 A 6/1994 Kittrell et al.
5,363,387 A 11/1994 Sinofsky
(Continued)

FOREIGN PATENT DOCUMENTS

CN 111526775 A 8/2020
CN 111565620 A 8/2020
(Continued)

OTHER PUBLICATIONS

Google Patents Translation of JP2008259595A (https://patents.google.com/patent/JP2008259595A/en?oq=JP+2008259595).
(Continued)

*Primary Examiner* — Timothy J Henn
(74) *Attorney, Agent, or Firm* — Terrence J. Edwards; TechLaw Ventures, PLLC

(57) ABSTRACT

Pulsed fluorescence imaging without input clock or data transmission clock is disclosed. A system includes an emitter for emitting pulses of electromagnetic radiation and an image sensor comprising a pixel array for sensing reflected electromagnetic radiation. The system includes a plurality of bidirectional data pads and a controller in communication with the image sensor. The system is such that at least a portion of the pulses of electromagnetic radiation emitted by the emitter comprises one or more of: electromagnetic radiation having a wavelength from about 770 nm to about 790 nm.

27 Claims, 32 Drawing Sheets

(51) Int. Cl.

| | | |
|---|---|---|
| *A61B 5/00* | (2006.01) | |
| *A61B 1/04* | (2006.01) | |
| *A61B 1/00* | (2006.01) | |
| *A61B 1/045* | (2006.01) | |
| *A61B 1/05* | (2006.01) | |
| *A61B 6/00* | (2006.01) | |
| *H03L 7/08* | (2006.01) | |
| *H03L 7/089* | (2006.01) | |
| *H03L 7/099* | (2006.01) | |
| *H04N 23/56* | (2023.01) | |
| *H04N 25/75* | (2023.01) | |
| *H04N 13/239* | (2018.01) | |

(52) U.S. Cl.
CPC ............... *A61B 1/045* (2013.01); *A61B 1/05* (2013.01); *A61B 5/0071* (2013.01); *A61B 6/50* (2013.01); *G01N 21/6428* (2013.01); *G01N 21/6456* (2013.01); *H03L 7/0807* (2013.01); *H03L 7/0891* (2013.01); *H03L 7/0991* (2013.01); *H04N 23/56* (2023.01); *H04N 25/75* (2023.01); *G01N 2021/6439* (2013.01); *H04N 13/239* (2018.05)

(58) Field of Classification Search
CPC ....... H04N 9/04521; H04N 2005/2255; H04N 23/665; H04N 23/56; H04N 25/75; H04N 23/125; H04N 23/555; H03L 7/0807; H03L 7/0891; H03L 7/0991; H03L 7/089; H03L 7/093; H03L 7/22; G01N 21/6428; G01N 21/6456; G01N 2021/6439; A61B 1/00006; A61B 1/043; A61B 1/045; A61B 1/05; A61B 5/0071; A61B 6/50; A61B 1/0655; A61B 1/00186; A61B 1/00194; A61B 1/0638
See application file for complete search history.

(56) References Cited

U.S. PATENT DOCUMENTS

| | | | |
|---|---|---|---|
| 5,749,830 A | | 5/1998 | Kaneko et al. |
| 6,110,106 A | | 8/2000 | MacKinnon et al. |
| 6,236,879 B1 | | 5/2001 | Konings |
| 6,300,638 B1 | | 10/2001 | Groger et al. |
| 6,603,116 B2 | | 8/2003 | Niito |
| 6,975,898 B2 | | 12/2005 | Seibel |
| 7,179,222 B2* | | 2/2007 | Imaizumi ............... A61B 1/046 |
| | | | 600/109 |
| 9,509,917 B2 | | 11/2016 | Blanquart et al. |
| 2001/0000317 A1 | | 4/2001 | Yoneya et al. |
| 2002/0123666 A1 | | 9/2002 | Matsumoto |
| 2002/0161282 A1 | | 10/2002 | Fulghum |
| 2003/0060683 A1 | | 3/2003 | Abe et al. |
| 2003/0100824 A1 | | 5/2003 | Warren et al. |
| 2004/0075883 A1 | | 4/2004 | Galvanauskas et al. |
| 2004/0186351 A1 | | 9/2004 | Imaizumi et al. |
| 2004/0234152 A1 | | 11/2004 | Liege et al. |
| 2005/0020926 A1 | | 1/2005 | Wiklof et al. |
| 2005/0027166 A1* | | 2/2005 | Matsumoto ........ A61B 1/00186 |
| | | | 977/852 |
| 2005/0107808 A1 | | 5/2005 | Evans et al. |
| 2006/0069314 A1 | | 3/2006 | Farr |
| 2006/0239723 A1 | | 10/2006 | Okuda et al. |
| 2006/0276966 A1 | | 12/2006 | Cotton et al. |
| 2007/0016077 A1 | | 1/2007 | Nakaoka et al. |
| 2007/0046778 A1 | | 3/2007 | Ishihara et al. |
| 2007/0081168 A1 | | 4/2007 | Johnston |
| 2007/0086495 A1 | | 4/2007 | Sprague et al. |
| 2007/0161907 A1 | | 7/2007 | Goldman et al. |
| 2007/0242330 A1 | | 10/2007 | Rosman et al. |
| 2007/0276234 A1 | | 11/2007 | Shahidi |
| 2008/0058629 A1 | | 3/2008 | Seibel et al. |
| 2008/0058638 A1* | | 3/2008 | Zhu ..................... G01N 21/6428 |
| | | | 600/425 |
| 2008/0081950 A1 | | 4/2008 | Koenig et al. |
| 2008/0177139 A1 | | 7/2008 | Courtney et al. |
| 2008/0177140 A1 | | 7/2008 | Cline et al. |
| 2008/0239070 A1 | | 10/2008 | Westwick et al. |
| 2009/0306478 A1 | | 12/2009 | Mizuyoshi |
| 2010/0049180 A1 | | 2/2010 | Wells et al. |
| 2010/0128109 A1 | | 5/2010 | Banks |
| 2010/0245639 A1 | | 9/2010 | Mori |
| 2010/0261958 A1 | | 10/2010 | Webb et al. |
| 2010/0277087 A1 | | 11/2010 | Ikeda |
| 2011/0087212 A1 | | 4/2011 | Aldridge et al. |
| 2011/0196355 A1 | | 8/2011 | Mitchell et al. |
| 2011/0213252 A1 | | 9/2011 | Fulghum |
| 2011/0280810 A1 | | 11/2011 | Hauger et al. |
| 2012/0010465 A1 | | 1/2012 | Erikawa et al. |
| 2012/0123205 A1 | | 5/2012 | Nie et al. |
| 2012/0294498 A1 | | 11/2012 | Popovic |
| 2013/0176395 A1 | | 7/2013 | Kazakevich |
| 2013/0211246 A1 | | 8/2013 | Parasher |
| 2013/0274596 A1 | | 10/2013 | Azizian et al. |
| 2013/0324797 A1 | | 12/2013 | Igarashi et al. |
| 2014/0073885 A1 | | 3/2014 | Frangioni |
| 2014/0111623 A1 | | 4/2014 | Zhao et al. |
| 2014/0160259 A1 | | 6/2014 | Blanquart et al. |
| 2014/0163319 A1 | | 6/2014 | Blanquart et al. |
| 2014/0271482 A1 | | 9/2014 | Low et al. |
| 2014/0275783 A1 | | 9/2014 | Blanquart |
| 2014/0276093 A1 | | 9/2014 | Zeien |
| 2014/0285645 A1 | | 9/2014 | Blanquart et al. |
| 2014/0300750 A1 | | 10/2014 | Nagamune |
| 2014/0336501 A1 | | 11/2014 | Masumoto |
| 2015/0073209 A1 | | 3/2015 | Ikeda |
| 2015/0109427 A1 | | 4/2015 | Wood et al. |
| 2015/0182118 A1 | | 7/2015 | Bradbury et al. |
| 2015/0205090 A1 | | 7/2015 | Jalali et al. |
| 2015/0223733 A1 | | 8/2015 | Al-Alusi |
| 2015/0305604 A1 | | 10/2015 | Melsky |
| 2015/0309284 A1 | | 10/2015 | Kagawa et al. |
| 2016/0006914 A1 | | 1/2016 | Neumann |
| 2016/0042513 A1 | | 2/2016 | Yudovksy |
| 2016/0062103 A1 | | 3/2016 | Yang et al. |
| 2016/0080665 A1 | | 3/2016 | Barnes et al. |
| 2016/0183775 A1 | | 6/2016 | Blanquart et al. |
| 2016/0195706 A1 | | 7/2016 | Fujii |
| 2017/0215711 A1 | | 8/2017 | Kobayashi et al. |
| 2017/0280029 A1 | | 9/2017 | Steiner |
| 2017/0280970 A1 | | 10/2017 | Sartor et al. |
| 2017/0360275 A1 | | 12/2017 | Yoshizaki |
| 2018/0000401 A1 | | 1/2018 | Kang et al. |
| 2018/0014000 A1 | | 1/2018 | Blanquart et al. |
| 2018/0183775 A1 | | 6/2018 | Malkapuram et al. |
| 2018/0310828 A1 | | 11/2018 | DiMaio et al. |
| 2019/0125454 A1 | | 5/2019 | Stokes et al. |
| 2019/0166322 A1* | | 5/2019 | Iwao ..................... H04N 25/75 |
| 2019/0170873 A1 | | 6/2019 | Reid |
| 2019/0191974 A1 | | 6/2019 | Talbert et al. |
| 2019/0191975 A1 | | 6/2019 | Talbert et al. |
| 2019/0191976 A1 | | 6/2019 | Talbert et al. |
| 2019/0191977 A1 | | 6/2019 | Talbert et al. |
| 2019/0191978 A1 | | 6/2019 | Talbert et al. |
| 2019/0197712 A1 | | 6/2019 | Talbert et al. |
| 2020/0400566 A1 | | 12/2020 | Talbert et al. |
| 2020/0400573 A1 | | 12/2020 | Talbert et al. |
| 2020/0400574 A1 | | 12/2020 | Talbert et al. |
| 2020/0403624 A1 | | 12/2020 | Talbert et al. |
| 2020/0404170 A1 | | 12/2020 | Talbert et al. |

FOREIGN PATENT DOCUMENTS

| | | |
|---|---|---|
| CN | 111601536 A | 8/2020 |
| JP | 2008259595 A | 10/2008 |
| WO | 2014018951 A1 | 1/2014 |
| WO | 2014134314 A1 | 9/2014 |
| WO | 2015077493 A1 | 11/2014 |
| WO | 2016203572 A1 | 12/2016 |
| WO | 2017201093 A1 | 5/2017 |
| WO | 2017223206 A1 | 12/2017 |

(56) References Cited

FOREIGN PATENT DOCUMENTS

| WO | 2018049215 A1 | 3/2018 |
|---|---|---|
| WO | 2019025533 A1 | 2/2019 |
| WO | 2019079010 A1 | 4/2019 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |
| WO | 2020257006 A1 | 12/2020 |
| WO | 2020257007 A1 | 12/2020 |
| WO | 2020257008 A1 | 12/2020 |
| WO | 2020257009 A1 | 12/2020 |
| WO | 2020257011 A1 | 12/2020 |

OTHER PUBLICATIONS

Google Patents Translation of WO2016203572 (https://patents.google.com/patent/JPWO2016203572A1/en?oq=WO2016203572).

* cited by examiner

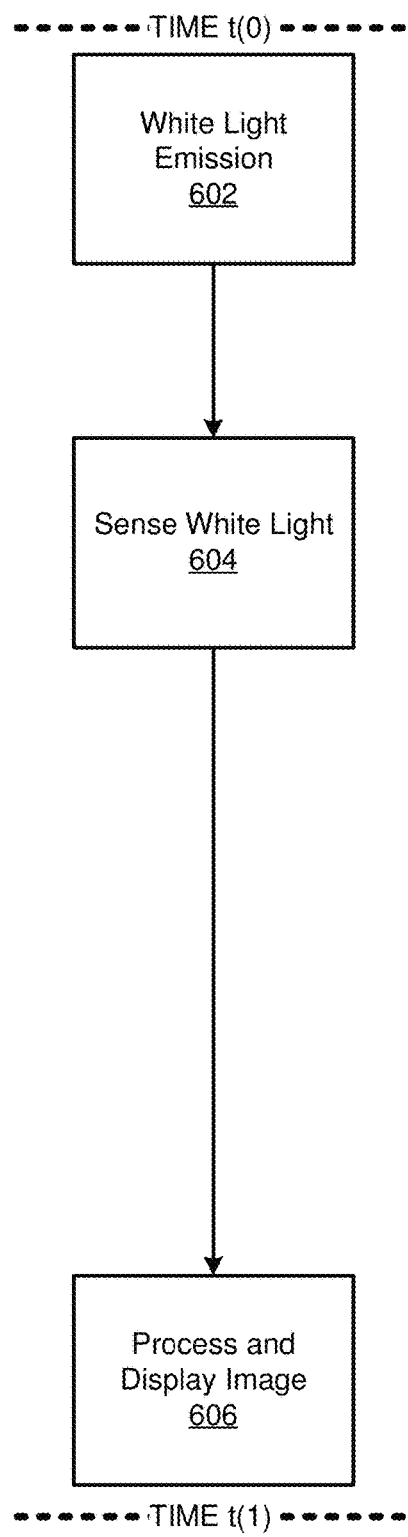
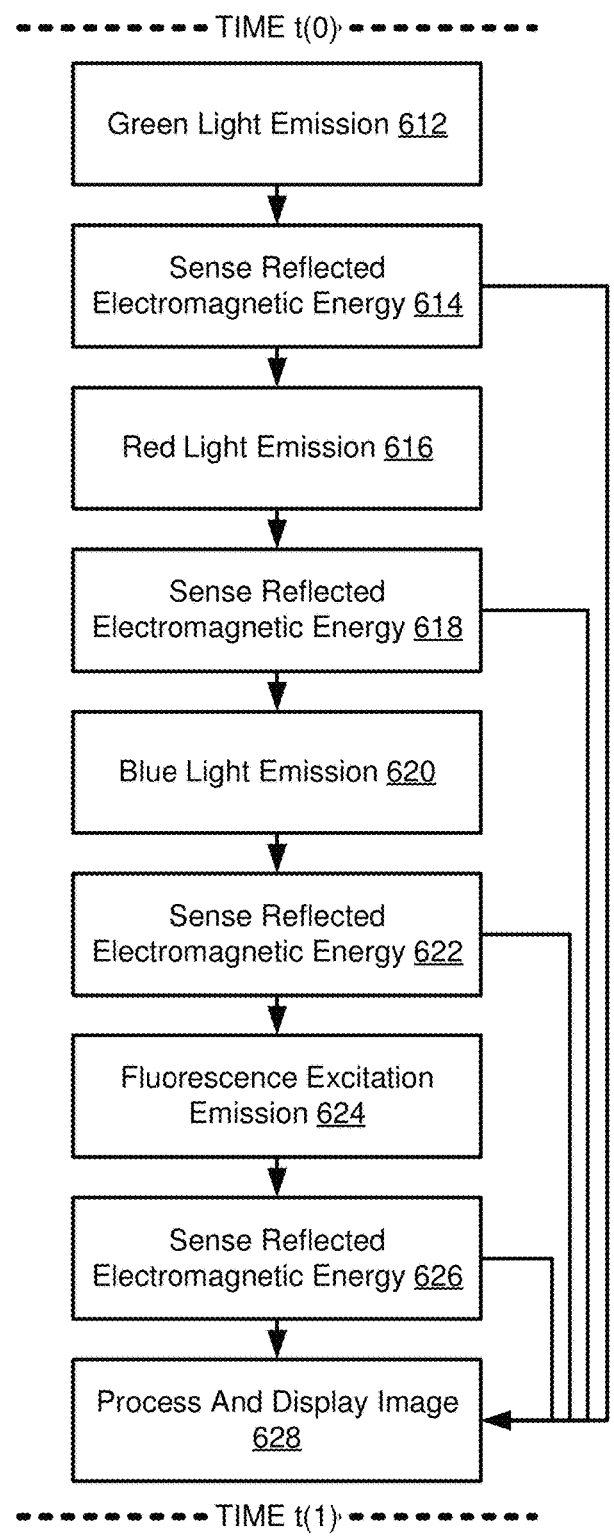
FIG. 6A
(Prior Art)
FIG. 6B

| | | |
|---|---|---|
| R_CLK | I | Recovered Clock. This is the input from the clock and data recovery (CDR) |
| REF_CLK | I | Reference Clock. This is the input from the known reference clock |
| CTL | I | Control inputs from the supervisory software. This sets the big and little push thresholds as well as the target frequency |
| PUSH | O | 0: don't push the frequency, 1: push the frequency |
| UP_DOWN | O | 0: if PUSH then push down, 1: if PUSH then push up |
| BIG_LITTLE | O | 0: if PUSH then push a little, 1: if PUSH then push big |

FIG. 19

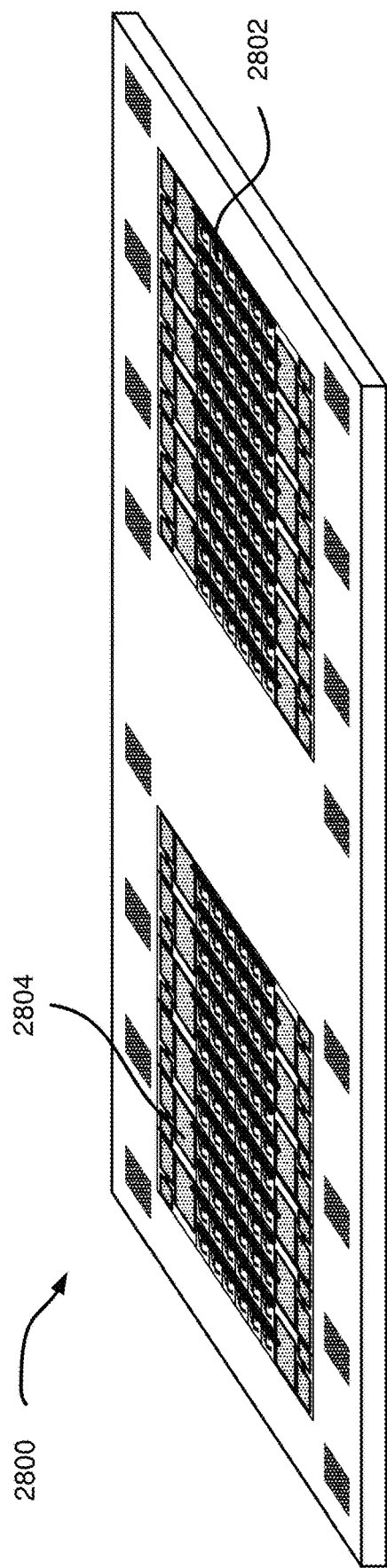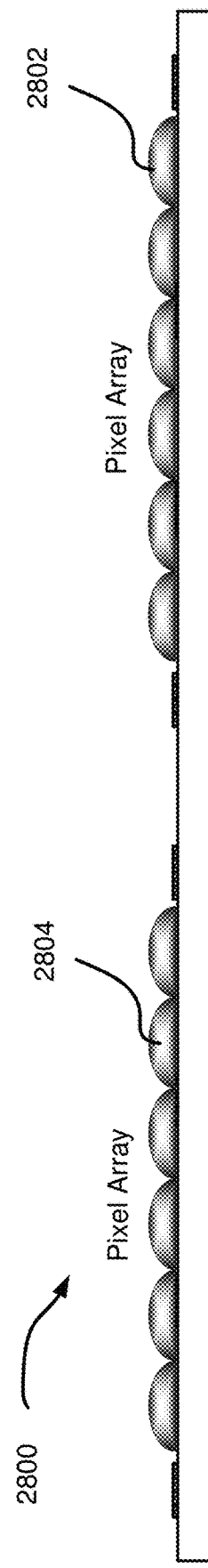
FIG. 28A
FIG. 28B

IMAGE SYNCHRONIZATION WITHOUT INPUT CLOCK AND DATA TRANSMISSION CLOCK IN A PULSED FLUORESCENCE IMAGING SYSTEM

CROSS-REFERENCE TO RELATED APPLICATIONS

This application claims the benefit of U.S. Provisional Patent Application No. 62/864,227, filed Jun. 20, 2019, titled "IMAGE SENSOR SYNCHRONIZATION WITHOUT INPUT CLOCK AND DATA TRANSMISSION CLOCK IN A HYPERSPECTRAL AND FLUORESCENCE IMAGING ENVIRONMENT," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This disclosure is directed to digital imaging and is particularly directed to fluorescence imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with fluorescence image data in addition to color image data. Fluorescence is the emission of light by a substance that has absorbed light or other electromagnetic radiation. Certain fluorescent materials "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the atom, molecule, or nanostructure. Fluorescence imaging has numerous practical applications, including mineralogy, gemology, medicine, spectroscopy for chemical sensors, detecting biological processes or signals, and others. Fluorescence can be used in biochemistry and medicine as a non-destructive means for tracking or analyzing biological molecules. Some fluorescent reagents or dyes can be configured to attach to certain types of tissue and thereby draw attention to that type of tissue.

However, fluorescence imaging requires specialized emissions of electromagnetic radiation and specialized imaging sensors capable of reading the specific relaxation wavelength for a specific fluorescent reagent. Different reagents or dyes are sensitive to different wavelengths of electromagnetic radiation and emit different wavelengths of electromagnetic radiation when fluoresced. A fluorescent imaging system may be highly specialized and tuned for a certain reagent or dye. Such imaging systems are useful for limited applications and are not capable of fluorescing more than one reagent or structure during a single imaging session. It is very costly to use multiple distinct imaging systems that are each configured for fluorescing a different reagent. Additionally, it may be desirable to administer multiple fluorescent reagents in a single imaging session and view the multiple reagents in a single overlaid image.

In light of the foregoing, described herein are systems, methods, and devices for fluorescent imaging in a light deficient environment. Such systems, methods, and devices may provide multiple datasets for identifying critical structures in a body and providing precise and valuable information about the body cavity.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIG. 19 is a table listing signals and parameters that may be used by a camera unit;

FIGS. 28A and 28B illustrate an implementation having a plurality of pixel arrays for producing a three-dimensional image in accordance with the principles and teachings of the disclosure.

DETAILED DESCRIPTION

Figure 1:
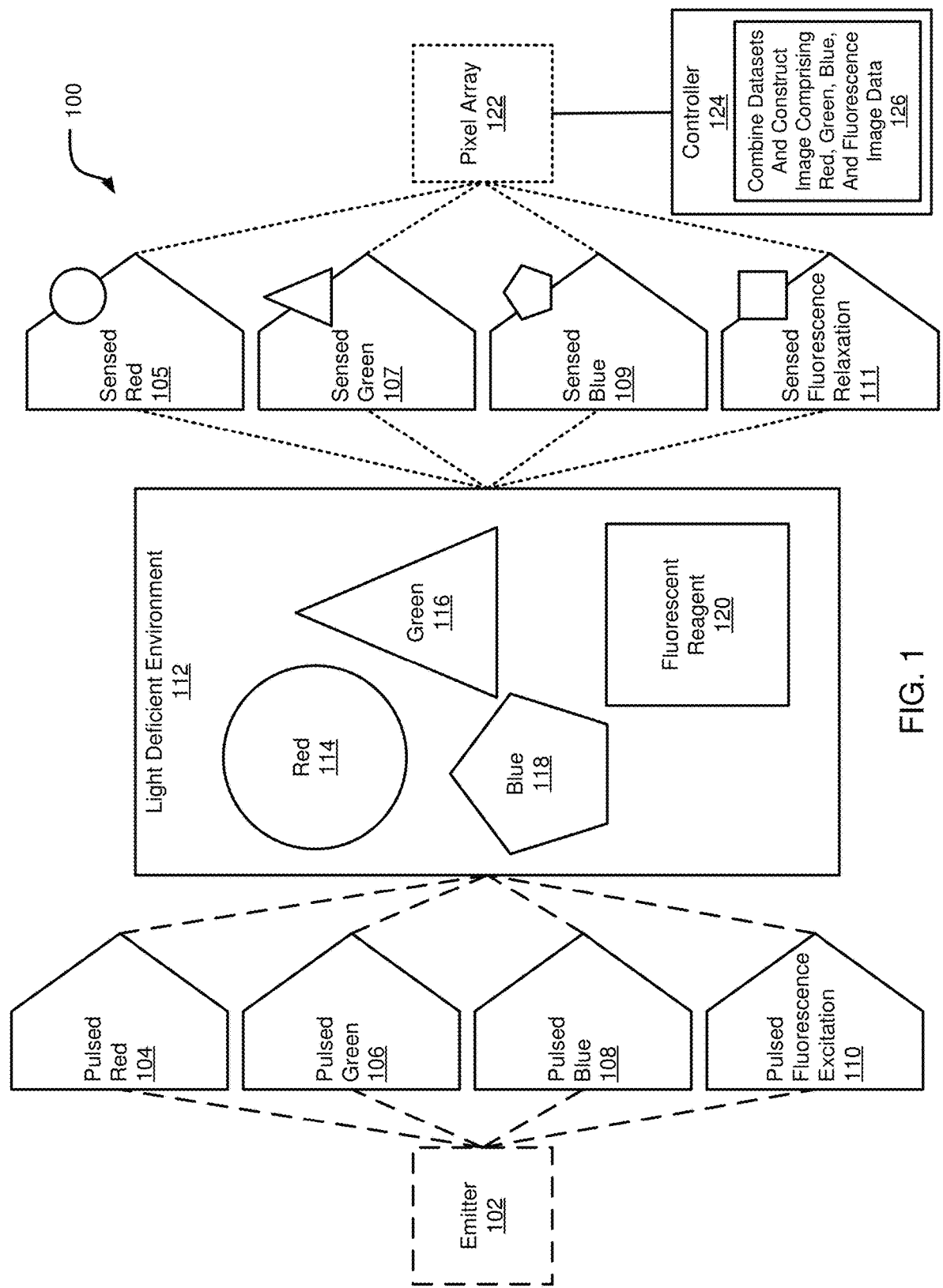
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for fluorescence and/or color imaging in a light deficient environment.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within a distal end of the endoscope itself. This provides greater optical simplicity when compared with implementations known in the art. However, an acceptable solution to this approach is by no means trivial and introduces its own set of engineering challenges.

For digital imaging systems, the final quality of a digital image depends on the engineering details of the electronic capture process that was used to generate the image. The perceived quality of an image is dependent on the signal to noise ratio (SNR), dynamic range (DR), spatial resolution, perception of visible unnatural artifacts, perception of spatial distortion, and color fidelity of the image. Each of these factors can be negatively impacted by decreasing the overall size of the image sensor. Therefore, in an effort to increase the perceived quality of a resultant image frame, traditional cameras known in the art include multiple image sensors or include an enlarged image sensor. For example, high-end cameras that can produce high resolution images typically include at least three monochrome sensors that are precisely coupled in an elaborate arrangement of prisms and filters. Another traditional solution is to use a single sensor with individual pixel-sized color filters fabricated on to the image sensor in a mosaic arrangement. The most popular mosaic arrangement is the Bayer pattern. An image sensor with a Bayer pattern can be inexpensive to fabricate but cannot achieve the image quality realized by the three-image sensor solution implemented in high-end cameras. An additional undesirable side effect of the Bayer pattern is that the color segmentation pattern introduces artifacts in the resultant image frames, and these artifacts can be especially noticeable around black and white edges.

There can be a noticeable loss to image quality when the overall size of an image sensor is minimized such that the image sensor can fit within the distal tip of an endoscope. The area of the pixel array of the image sensor can be reduced by reducing the number of pixels and/or the sensing area of each individual pixel. Each of these modifications impacts the resolution, sensitivity, and dynamic range of the resultant images. Traditional endoscopic imaging systems are geared toward sensing steady broadband illumination and providing color information by virtue of segmented pixel arrays such as the Bayer pattern array. In light of the deficiencies associated with segmented pixel arrays, disclosed herein are alternative systems and methods that use a monochromatic (may be referred to as "color agnostic") pixel array that does not include individual pixel filters. In the embodiments disclosed herein, the color information is provided by pulsing an emitter with different wavelengths of electromagnetic radiation. The pulsed imaging system disclosed herein can generate color images with fluorescence imaging data overlaid thereon.

In an embodiment, the color information is determined by capturing independent exposure frames in response to pulses of different wavelengths of electromagnetic radiation. The alternative pulses may include red, green, and blue wavelengths for generating an RGB image frame consisting of a red exposure frame, a green exposure frame, and a blue exposure frame. The image frame may further include data from a fluorescence exposure frame overlaid on the RGB image frame. The fluorescence pulse may include one or more pulses of electromagnetic radiation for exciting a fluorescent reagent or dye. In an embodiment, the fluorescence emission includes one or more of electromagnetic radiation having a wavelength from about 770 nm to about 790 nm and/or electromagnetic radiation having a wavelength from about 795 nm to about 815 nm. It should be appreciated the fluorescence emission may include any suitable wavelengths of electromagnetic radiation for fluorescing a reagent or dye.

In an embodiment, the overall size of the image sensor is further reduced by reducing the number of pads on the image sensor chip. A significant portion of total chip area is consumed by individual bond pads on the image sensor chip. Each bond pad provides power and input/output signals to and from the image sensor chip. In the systems and methods disclosed herein, the imaging sensor pad count is reduced by negating the need for an output clock or an input clock. An embodiment of the disclosure causes an imaging sensor of an endoscope to issue a continuous stream of ones (is) and zeroes (Os) on its data port(s) upon power up. This causes a data receiver within the support electronics of the endoscope to synchronize using a Clock Data Recovery (CDR) circuit by way of clock training. In an embodiment, the continuous stream of ones and zeroes is enabled during normal operation by toggling one configuration register bit. Once the data receiver locks into this training pattern, normal sensor imaging operation may proceed. The lock on the training pattern may be maintained by avoiding long periods without transmissions by including a single invert bit for the digital value issued for each pixel of the image sensor.

In an embodiment, the data generated by the image sensor is synchronized without an output clock. Traditional high speed data transmission is accompanied by a clock for synchronization purposes. In the embodiments disclosed herein, the clock signal is embedded within the data stream itself by way of clock encoding. At the receiving end, the data stream is decoded to extract the clock and latch the data. This embodiment negates the need for output clock pads on the image sensor chip and thereby reduces the overall size of the image sensor. In an embodiment, the endoscopic imaging system deploys the Clock Data Recovery (CDR) system to correctly latch incoming data. The CDR system uses an internal phase lock loop (PLL) to lock incoming data and latch the incoming data. The locking process uses data transitions for the phase lock loop to converge. In an embodiment, a minimum number of transitions for initial locking (and re-locking) is specified along with a maximum number of consecutive allowed bits without transition. This may be required for the phase lock loop to remain locked.

In some instances, it is desirable to generate endoscopic imaging with multiple data types or multiple images overlaid on one another. For example, it may be desirable to generate a color (Red Green Blue "RGB") image that further includes fluorescence imaging data overlaid on the RGB image. An overlaid image of this nature may enable a medical practitioner or computer program to identify critical body structures based on the fluorescence imaging data. Historically, this would require the use of multiple sensor systems including an image sensor for color imaging and one or more additional image sensors for fluorescence imaging. In such systems, the multiple image sensors would have multiple types of pixel sensors that are each sensitive to distinct ranges of electromagnetic radiation. In systems known in the art, this includes the three separate types of pixel sensors for generating an RGB color image along with additional pixel sensors for generating the fluorescence image data at different wavelengths of the electromagnetic spectrum. These multiple different pixel sensors consume a prohibitively large physical space and cannot be located at a distal tip of the endoscope. In systems known in the art, the camera or cameras are not placed at the distal tip of the endoscope and are instead placed in an endoscope handpiece or robotic unit. This introduces numerous disadvantages and causes the endoscope to be very delicate. The delicate endoscope may be damaged and image quality may be degraded when the endoscope is bumped or impacted during use. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Fluorescence Imaging

The systems, methods, and devices disclosed herein provide means for generating fluorescence imaging data in a light deficient environment. The fluorescence imaging data may be used to identify certain materials, tissues, components, or processes within a body cavity or other light deficient environment. In certain embodiments, fluorescence imaging is provided to a medical practitioner or computer-implemented program to enable the identification of certain structures or tissues within a body. Such fluorescence imaging data may be overlaid on black-and-white or RGB images to provide additional information and context.

Fluorescence is the emission of light by a substance that has absorbed light or other electromagnetic radiation. Certain fluorescent materials may "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance. However, when the absorbed electromagnetic radiation is intense, it is possible for one electron to absorb two photons. This two-photon absorption can lead to emission of radiation having a shorter wavelength, and therefore higher energy, than the absorbed radiation. Additionally, the emitted radiation may also be the same wavelength as the absorbed radiation.

Fluorescence imaging has numerous practical applications, including mineralogy, gemology, medicine, spectroscopy for chemical sensors, detecting biological processes or signals, and so forth. Fluorescence may particularly be used in biochemistry and medicine as a non-destructive means for tracking or analyzing biological molecules. The biological molecules, including certain tissues or structures, may be tracked by analyzing the fluorescent emission of the biological molecules after being excited by a certain wavelength of electromagnetic radiation. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of electromagnetic radiation. Different reagents or dyes may include different molecules, proteins, and/or quantum dots that will fluoresce at particular wavelengths of electromagnetic radiation. Thus, it may be necessary to excite the reagent or dye with a specialized band of electromagnetic radiation to achieve fluorescence and identify the desired tissue, structure, or process in the body.

Fluorescence imaging may provide valuable information in the medical field that may be used for diagnostic purposes and/or may be visualized in real-time during a medical procedure. Specialized reagents or dyes may be administered to a body to fluoresce certain tissues, structures, chemical processes, or biological processes. The fluorescence of the reagent or dye may highlight body structures such as blood vessels, nerves, particular organs, and so forth. Additionally, the fluorescence of the reagent or dye may highlight conditions or diseases such as cancerous cells or cells experiencing a certain biological or chemical process that may be associated with a condition or disease. The fluorescence imaging may be used in real-time by a medical practitioner or computer program for differentiating between, for example, cancerous and non-cancerous cells during a surgical tumor extraction. The fluorescence imaging may further be used as a non-destructive means for tracking and visualizing over time a condition in the body that would otherwise not be visible by the human eye or distinguishable in an RGB image.

The systems, methods, and devices for generating fluorescence imaging data may be used in coordination with reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The endoscopic imaging system disclosed herein is used to excite and fluoresce the reagent or dye. The fluorescence of the reagent or dye is captured by the endoscopic imaging system to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the endoscopic imaging system emits each of the applicable wavelengths to fluoresce each of the applicable reagents or dyes. This may negate the need to perform individual imaging procedures for each of the plurality of reagents or dyes.

Imaging reagents can enhance imaging capabilities in pharmaceutical, medical, biotechnology, diagnostic, and medical procedure industries. Many imaging techniques such as X-ray, computer tomography (CT), ultrasound, magnetic resonance imaging (MRI), and nuclear medicine, mainly analyze anatomy and morphology and are unable to detect changes at the molecular level. Fluorescent reagents, dyes, and probes, including quantum dot nanoparticles and fluorescent proteins, assist medical imaging technologies by providing additional information about certain tissues, structures, chemical processes, and/or biological processes that are present within the imaging region. Imaging using fluorescent reagents enables cell tracking and/or the tracking of certain molecular biomarkers. Fluorescent reagents may be applied for imaging cancer, infection, inflammation, stem cell biology, and others. Numerous fluorescent reagents and dyes are being developed and applied for visualizing and tracking biological processes in a non-destructive manner. Such fluorescent reagents may be excited by a certain wavelength or band of wavelengths of electromagnetic radiation. Similarly, those fluorescent reagents may emit relaxation energy at a certain wavelength or band of wavelengths when fluorescing, and the emitted relaxation energy may be read by a sensor to determine the location and/or boundaries of the reagent or dye.

In an embodiment of the disclosure, an endoscopic imaging system pulses electromagnetic radiation for exciting an electron in a fluorescent reagent or dye. The endoscopic imaging system may pulse multiple different wavelengths of electromagnetic radiation for fluorescing multiple different reagents or dyes during a single imaging session. The endoscope includes an image sensor that is sensitive to the relaxation wavelength(s) of the one or more reagents or dyes. The imaging data generated by the image sensor can be used to identify a location and boundary of the one or more reagents or dyes. The endoscope system may further pulse electromagnetic radiation in red, green, and blue bands of visible light such that the fluorescence imaging can be overlaid on an RGB video stream.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a fluorescence image. The pixels may be color agnostic such that each pixel generates data for each pulse of electromagnetic radiation, including pulses for red, green, and blue visible light wavelengths along with other wavelengths used for fluorescence imaging.

A system of the disclosure is an endoscopic imaging system for use in a light deficient environment. The system includes an endoscope comprising an image sensor, wherein the image sensor is configured to sense reflected electromagnetic radiation for generating a plurality of exposure frames that can be combined to generate an RGB image frame with fluorescence data overlaid thereon. The system includes an emitter for emitting pulses of electromagnetic radiation. The system includes a controller (may alternatively be referred to as a "control circuit" in electronic communication with the image sensor and the emitter. The controller controls a duty cycle of the emitter in response to signals corresponding to a duty cycle of the emitter. The image sensor includes bidirectional pads that can send and receive information. The bidirectional pads of the image sensor operate in a frame period divided into three defined states, including a rolling readout state, a service line state, and a configuration state. The system includes an oscillator disposed in the controller and a frequency detector connected to the controller. The frequency detector controls a clock frequency of the image sensor in response to signals from the controller that correspond to the frequency of the oscillator. The system is such that clock signal data is transmitted from the bidirectional pads of the image sensor to the controller during the service line phase and the configuration phase. The system is such that exposure frames are synchronized without the use of an input clock or a data transmission clock.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with fluorescence imaging data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in image data sensed by the pixel array 122.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108, and a fluorescence excitation 110 wavelength. The fluorescence excitation 110 wavelength may include a plurality of different partitions of electromagnetic radiation that are selected to fluoresce a plurality of fluorescent reagents that are present within the light deficient environment 112. The fluorescent excitation 110 wavelength may be selected to fluoresce a particular fluorescent reagent that is present in the light deficient environment 112.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting pulsed fluorescence excitation 110 wavelength(s) of electromagnetic radiation for identifying a fluorescent reagent 120 within the light deficient environment 112. The fluorescent reagent 120 is identified by exciting the fluorescent reagent 120 with the pulsed fluorescence excitation 110 light and then sensing (by the pixel array 122) the fluorescence relaxation 111 wavelength for that particular fluorescent reagent 120. The emitter 102 is capable of emitting the pulsed red 104, pulsed green 106, pulsed blue 108, and pulsed fluorescence excitation 110 wavelengths in any desired sequence.

The pixel array 122 senses reflected electromagnetic radiation. Each of the sensed red 105, the sensed green 107, the sensed blue 109, and the sensed fluorescence relaxation 111 data can be referred to as an "exposure frame." Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed fluorescence relaxation 111 exposure frame identifying the fluorescent reagent 120 and corresponding in time with the pulsed fluorescence excitation 110 wavelength(s) of light.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, fluorescence imaging responsive to the pulsed excitation 110 wavelength between 770 nm and 790 nm and between 795 nm and 815 nm.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes a fluorescent reagent 120. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

Figure 2:
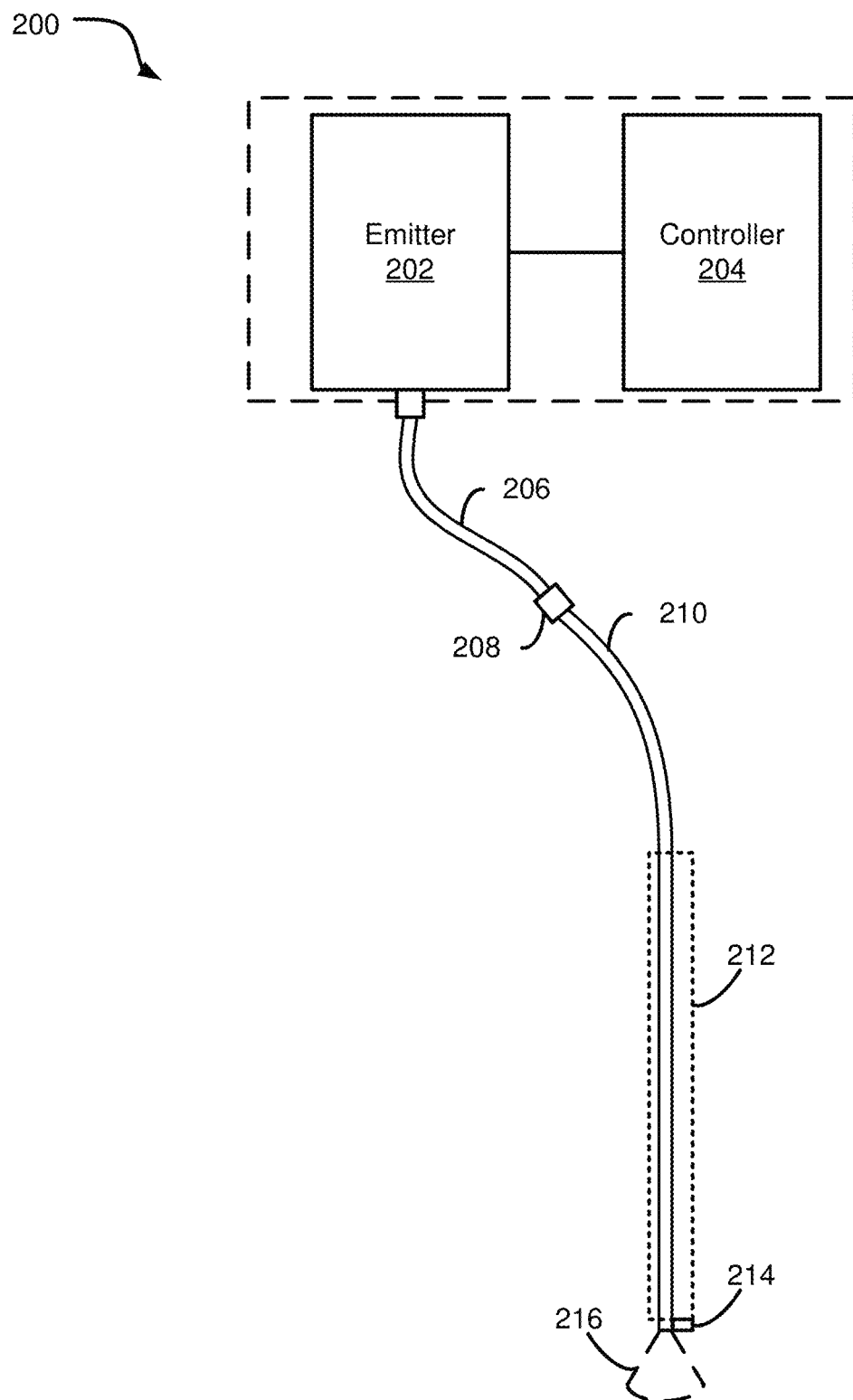
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, laser mapping pulsing schemes, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera control unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
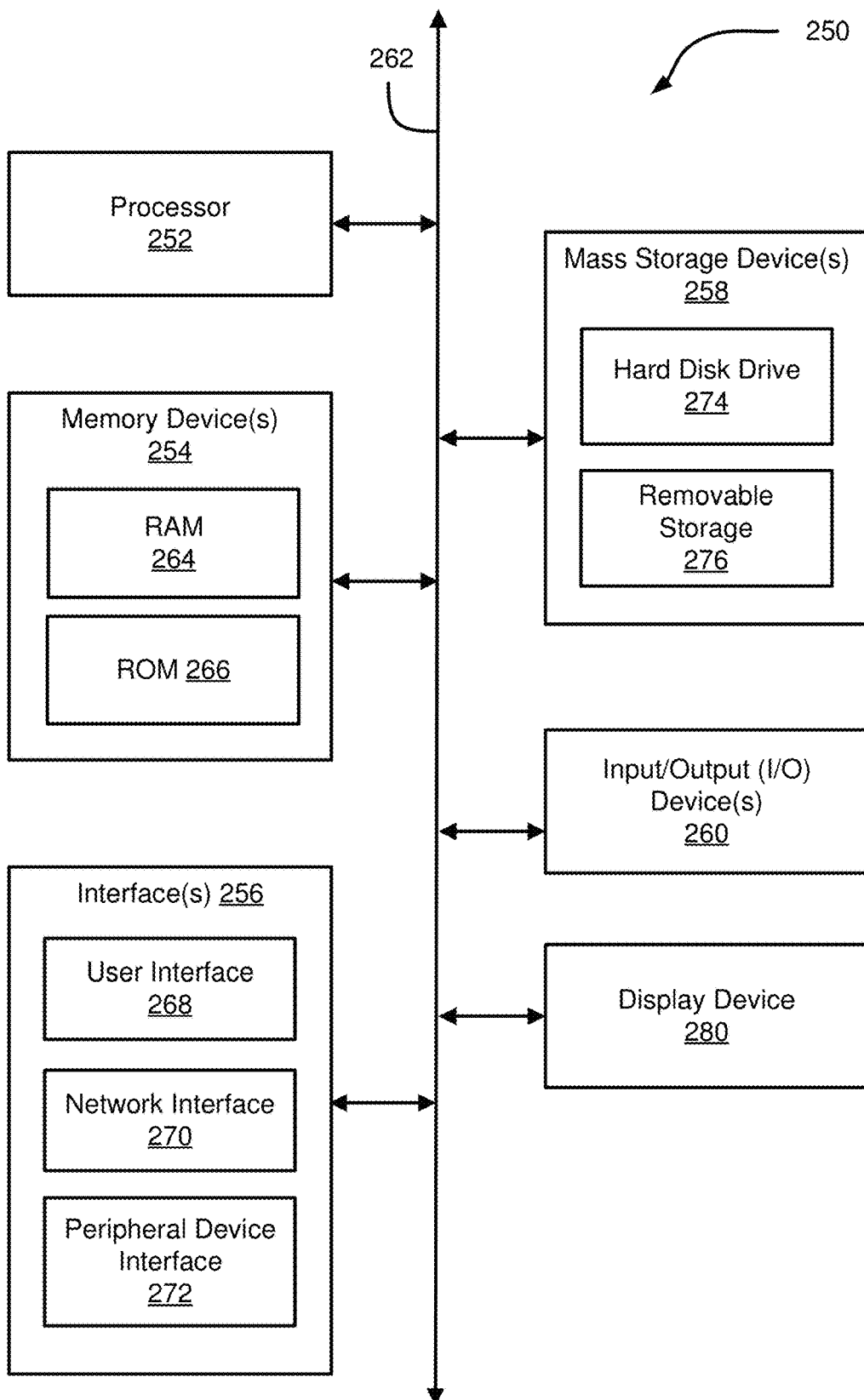
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera control unit, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
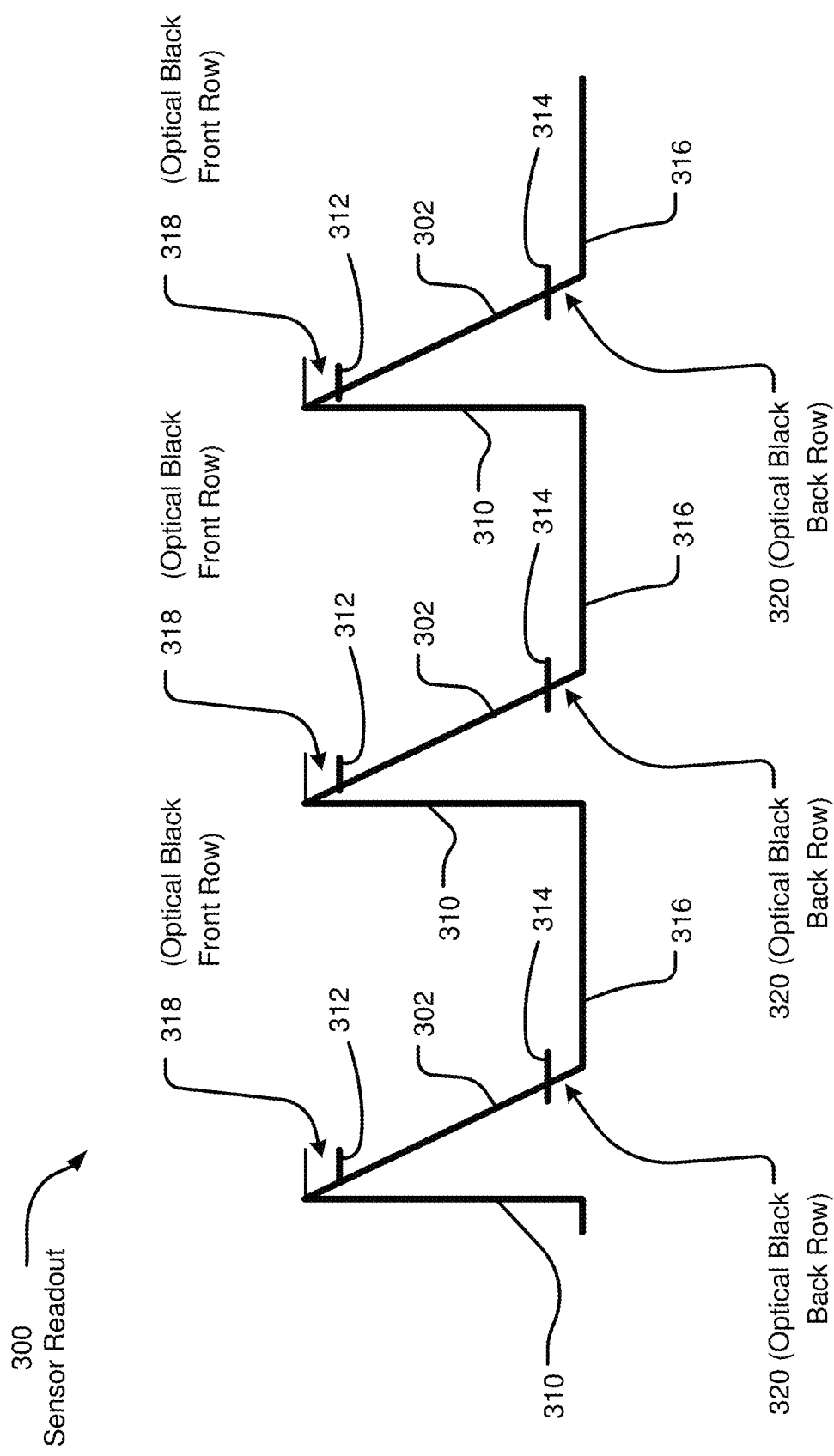
FIGS. 3A to 3D are illustrations of the operational cycles of a sensor used to construct an exposure frame.

FIG. 3A illustrates the operational cycles of a sensor used in rolling readout mode or during the sensor readout 300. The frame readout period may start at and may be represented by vertical line 310. The readout period 302 is represented by the diagonal or slanted line. The sensor may be read out on a row by row basis, the top of the downwards slanted edge being the sensor top row 312 and the bottom of the downwards slanted edge being the sensor bottom row 314. The time between the last row readout and the next readout period may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

Figure 3B:
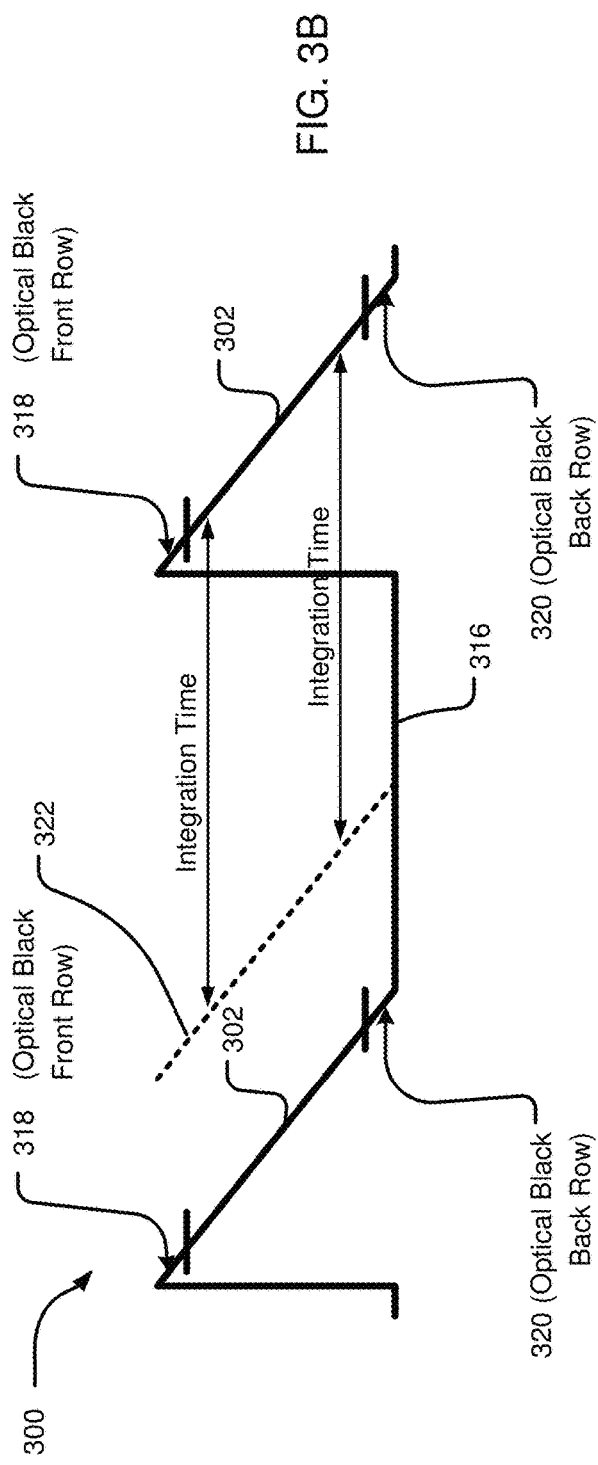

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout period. The position of the electronic shutter 322 can be moved between two readout periods 302 to control the pixel saturation for a given amount of light. It should be noted that this technique allows for a constant integration time between two different lines but introduces a delay when moving from top to bottom rows.

Figure 3C:
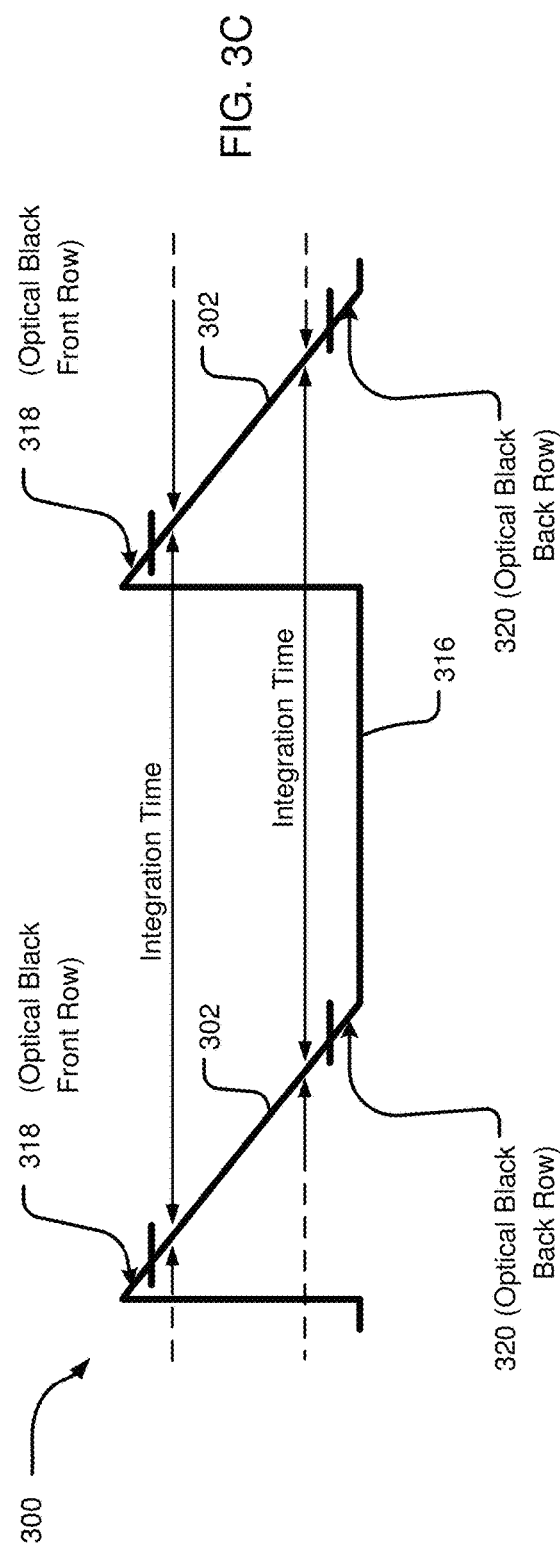

FIG. 3C illustrates the case where the electronic shutter 322 has been removed. In this configuration, the integration of the incoming light may start during the readout period 302 and may end at the next readout period 302, which also defines the start of the next integration.

Figure 3D:
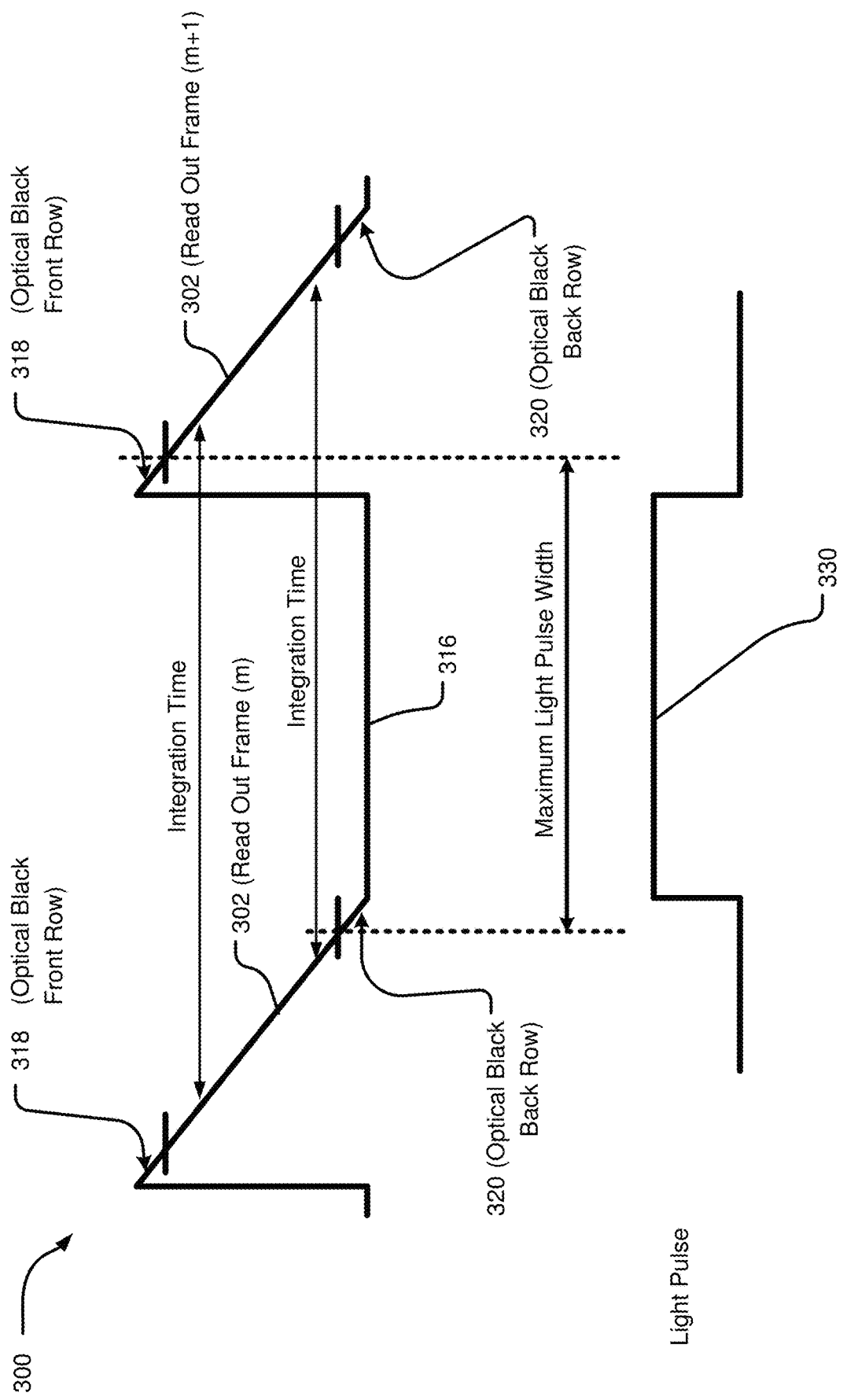

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
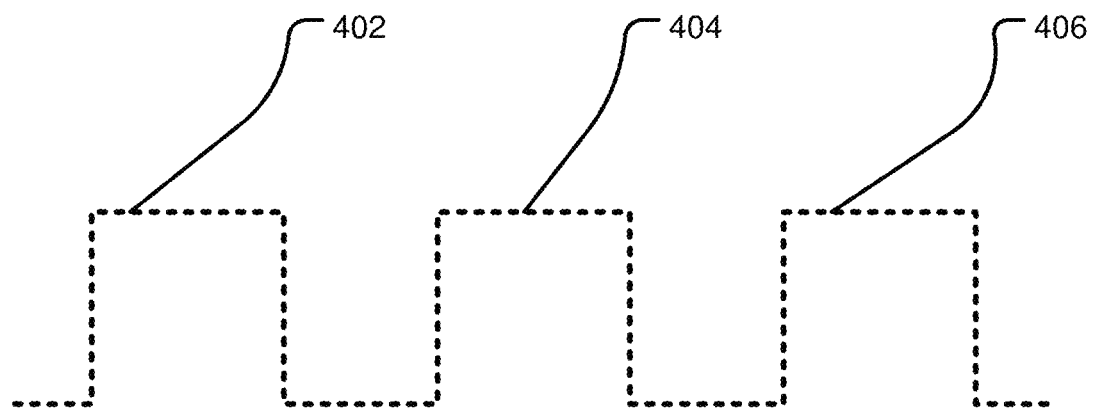
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking period 316 of the sensor operation cycle. In an embodiment, the emitter may pulse for a duration that is during portions of two or more sensor operational cycles. In an embodiment, the emitter may begin a pulse during the blanking period 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
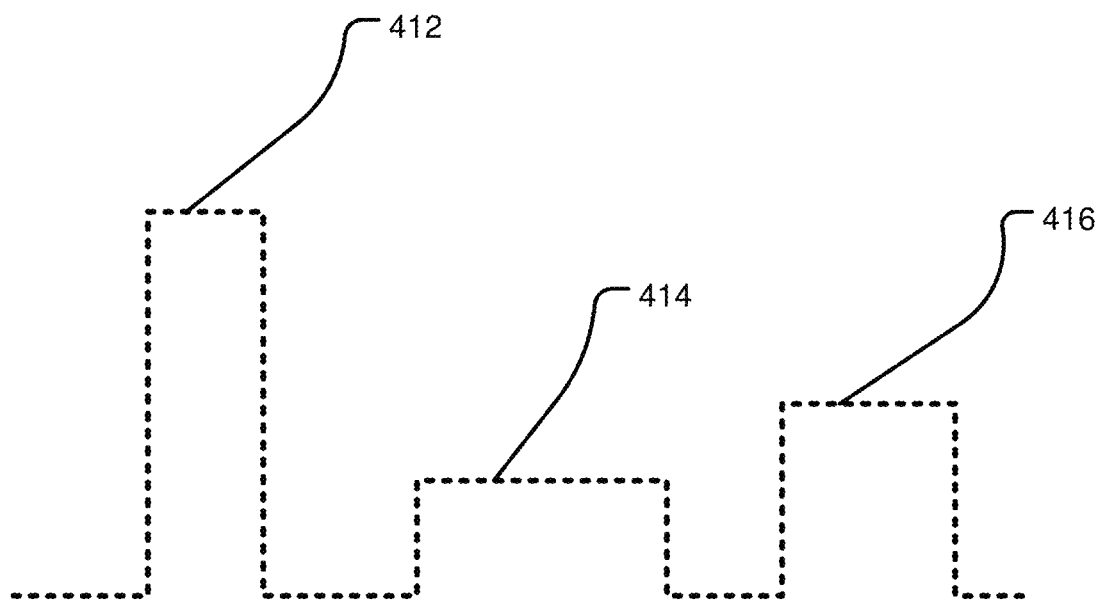
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
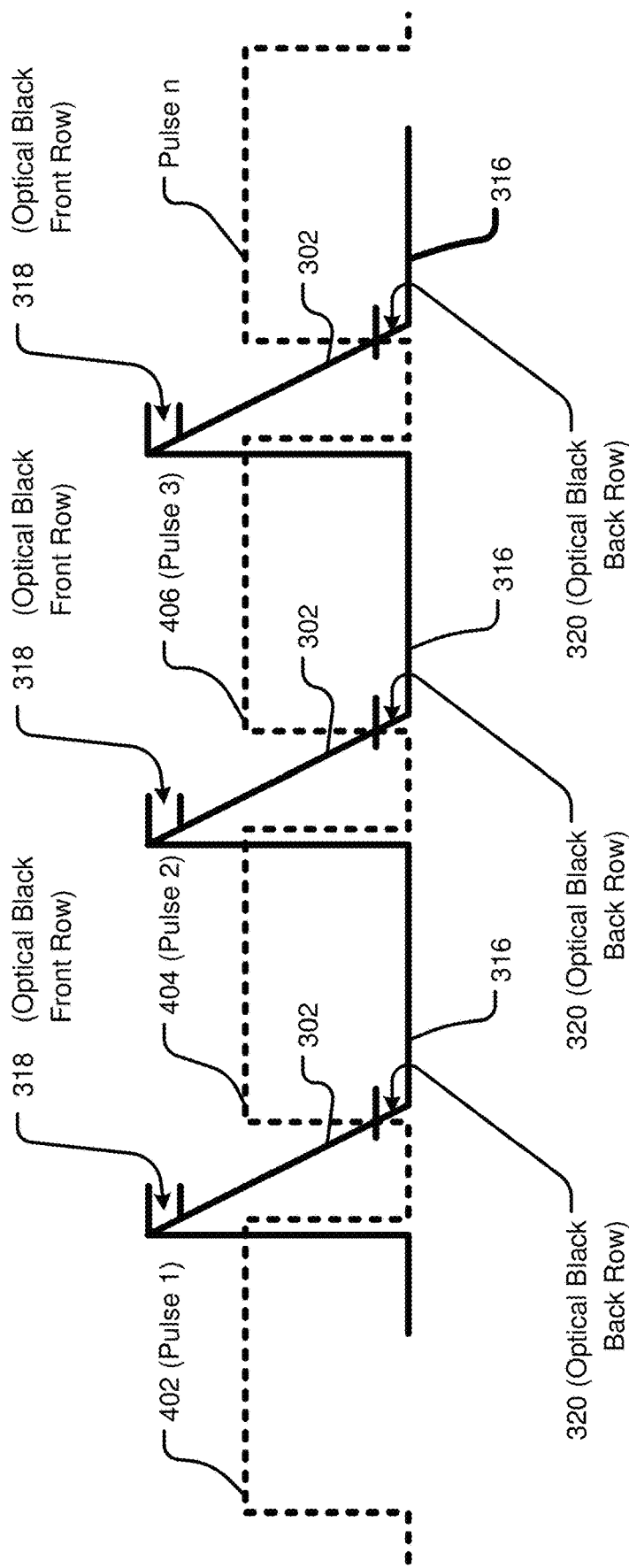
FIG. 5 is a graphical representation of an embodiment of the disclosure combining the operational cycles of a sensor, the electromagnetic emitter, and the emitted electromagnetic pulses of FIGS. 3A-4B, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 302. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a fluorescence excitation wavelengths 624 and sensing reflected electromagnetic energy 626 subsequent to each of the one or more emissions of fluorescence excitation wavelengths of electromagnetic radiation 624. The image is processed and displayed at 628 based on each of the sensed reflected electromagnetic energy instances 614, 618, 622, and 626.

The process illustrated in FIG. 6B provides a higher resolution image and provides a means for generating an RGB image that further includes fluorescence imaging data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
   i. Green pulse;
   ii. Red pulse;
   iii. Blue pulse;
   iv. Green pulse;
   v. Red pulse;
   vi. Blue pulse;
   vii. Fluorescence excitation pulse;
   viii. (Repeat)

As can be seen in the example, a fluorescence excitation partition may be pulsed at a rate differing from the rates of the other partition pulses. This may be done to emphasize a certain aspect of the scene, with the fluorescence imaging data simply being overlaid with the other data in the video output to make the desired emphasis. It should be noted that the addition of a fluorescence partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (fluorescence excitation in the above example), would result in an increase of less than 20% of the cycling speed of the sensor to accommodate the irregular partition sampling.

In various embodiments, the pulse cycle pattern may further include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
   i. 770±20 nm;
   ii. 770±10 nm;
   iii. 770±5 nm;
   iv. 790±20 nm;
   v. 790±10 nm;
   vi. 790±5 nm;
   vii. 795±20 nm;
   viii. 795±10 nm;
   ix. 795±5 nm;
   x. 815±20 nm;
   xi. 815±10 nm;
   xii. 815±5 nm;
   xiii. 770 nm to 790 nm; and/or
   xiv. 795 nm to 815 nm.

Figure 7A:
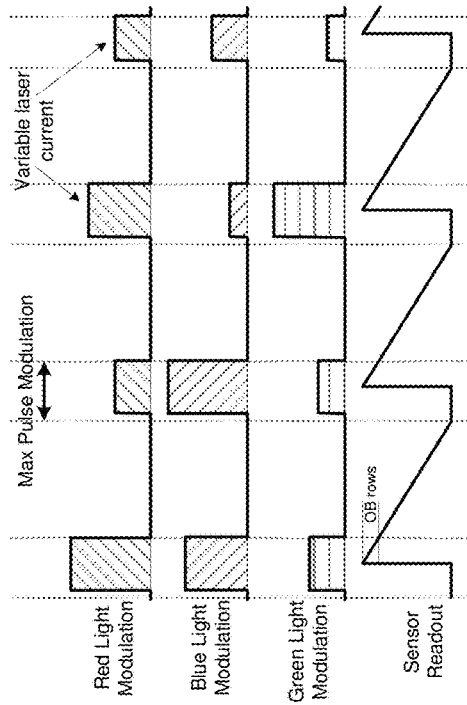
FIGS. 7A-7E illustrate schematic views of the processes over an interval of time for recording a frame of video for both full spectrum light and partitioned spectrum light.
Figure 7C:
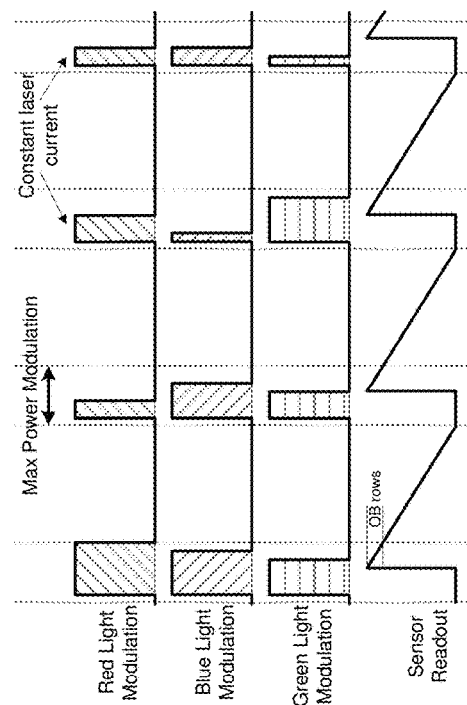
Figure 7B:
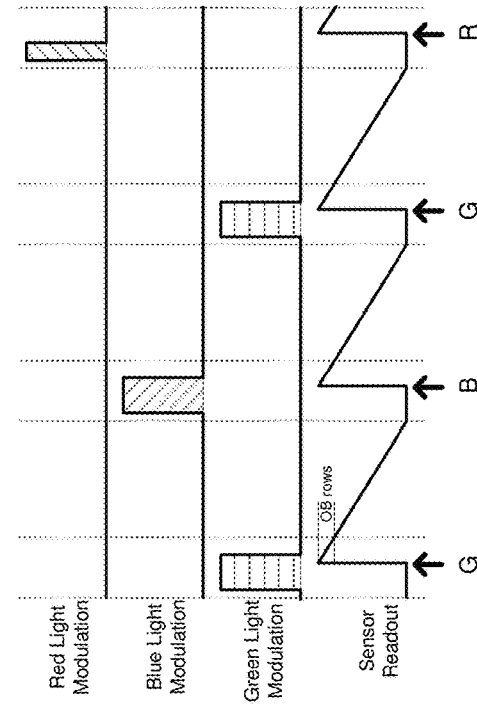

The partition cycles may be divided so as to accommodate or approximate various imaging and video standards. In an embodiment, the partition cycles may comprise pulses of electromagnetic energy in the Red, Green, and Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
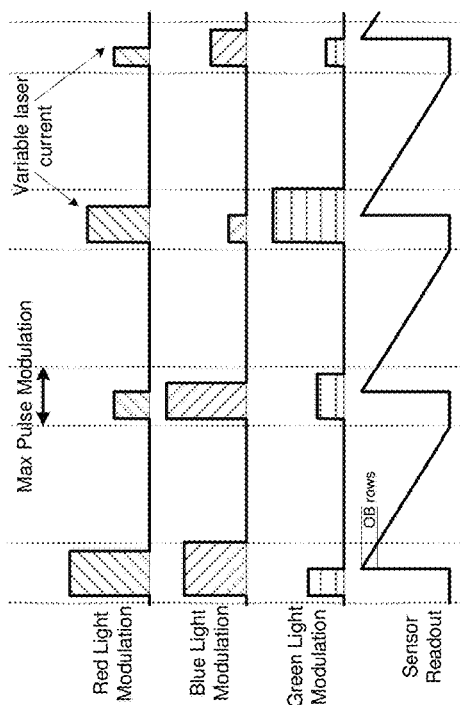

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
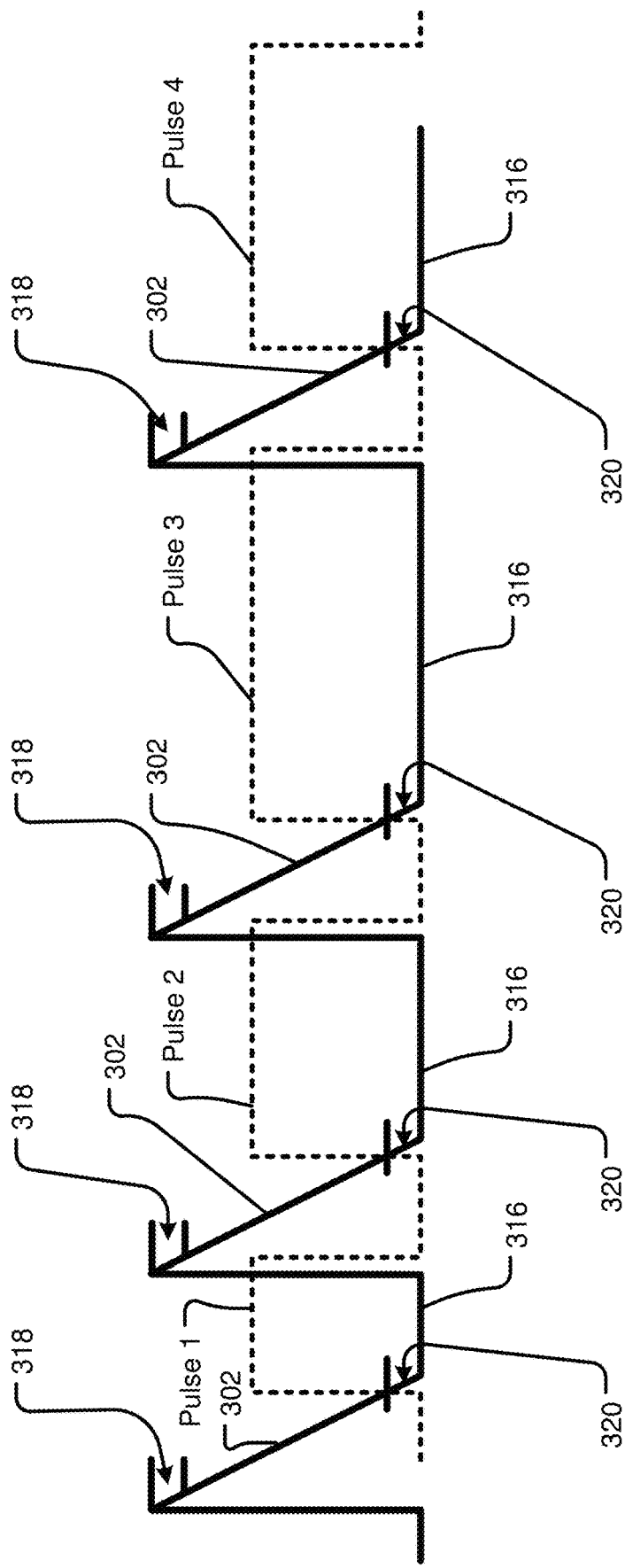

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking times with a repeating pattern of two or three or four or n frames. In FIG. 7E, four different light pulses are illustrated, and Pulse 1 may repeat for example after Pulse 4 and may have a pattern of four frames with different blanking times. This technique can be used to place the most powerful partition on the smallest blanking time and therefore allow the weakest partition to have wider pulse on one of the next frames without the need of increasing the readout speed. The reconstructed frame can still have a regular pattern from frame to frame as it is constituted of many pulsed frames.

Figure 8:
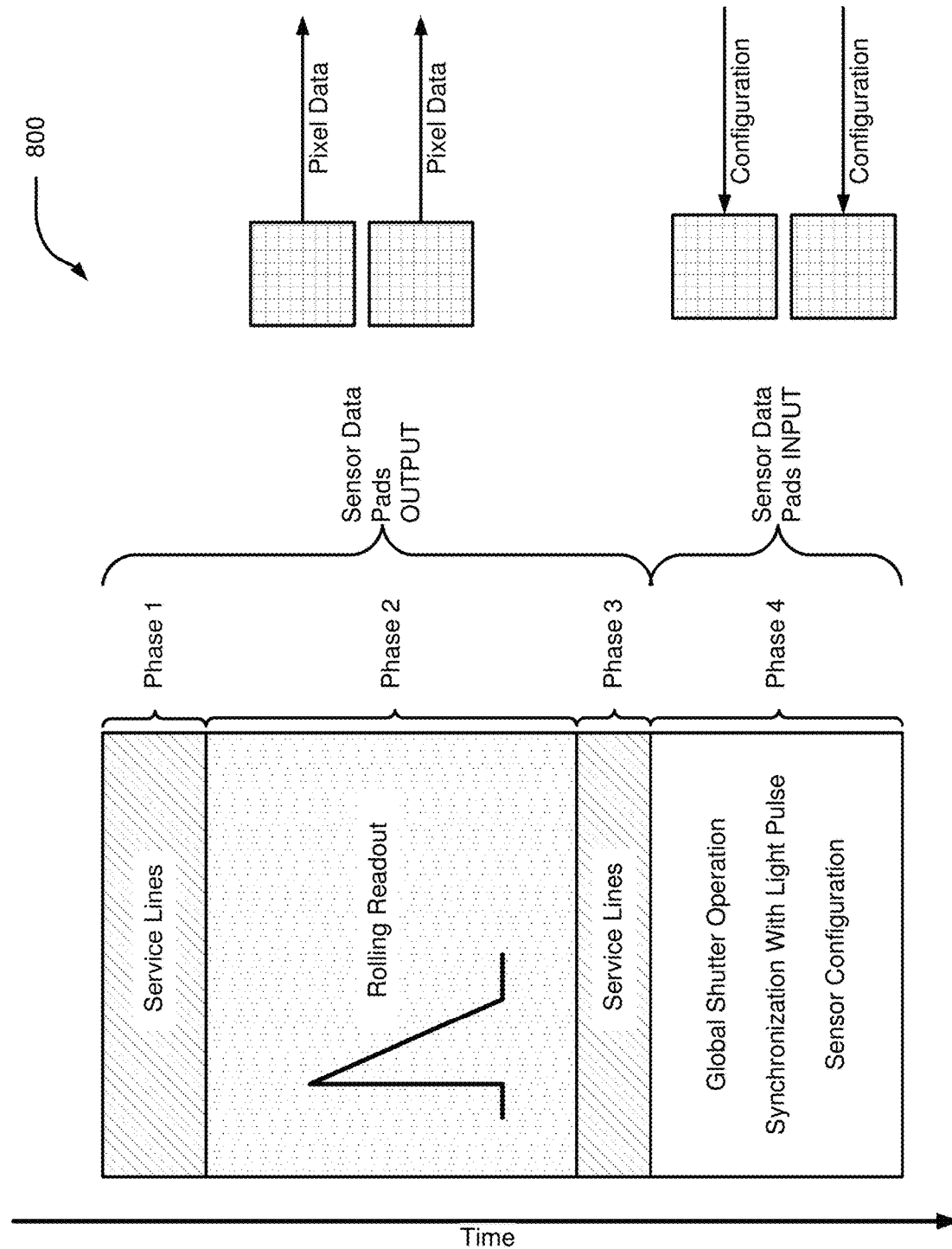
FIG. 8 is a schematic diagram of a regular operation sequence for an image sensor.

FIG. 8 is a schematic diagram of an embodiment of a regular operation sequence 800 for an image sensor. In an embodiment, one iteration of the regular operation sequence 800 results in one exposure frame generated by the image sensor. In an alternative embodiment, one iteration of the regular operation sequence 800 results in multiple exposure frames generated by the image sensor. The regular operation sequence 800 may be implemented for the purpose of endoscopic imaging in the presence of controlled, pulsed illumination. Each frame period may comprise four distinct phases, which may be optimized for monochrome light pulsing and multiple pixel illuminations.

The example regular operation sequence 800 illustrated in FIG. 8 includes four phases, including phase 1, phase 2, phase 3, and phase 4. During phases 1 and 3, data is issued from the image sensor through sensor data pads. These "service line" periods may be used for internal and external monitoring and for encoding certain types of non-pixel data within the line. This data can be used to synchronize the image sensor chip with the camera system and can further be used for data locking. In an embodiment, imaging data from the pixel array is not output during the service line periods.

During phase 2, the sensor rolling readout is issued from the image sensor through the sensor data pads. Phase 2 includes the synchronization and readout of physical pixels in the pixel array of the image sensor during a "rolling readout" period. The rolling readout includes imaging data sensed by the pixel array and results in one or more exposure frames being generated by the image sensor.

During phase 4, image sensor configurations are received by the image sensor through the sensor data pads. Phase 4 may be referred to as the configuration phase. During phase 4, the data lines are reversed to accept incoming configuration commands rather than issue exiting pixel data or non-pixel data. There is a risk that during phase 4, the Clock Data Recovery (CDR) circuit in the camera unit will become unlocked and the image sensor will not send any data transitions during a defined period. The service lines of phase 1 may be used to send a continuous stream of data transitions, however, to re-lock the camera unit CDR circuit if required.

Figure 9:
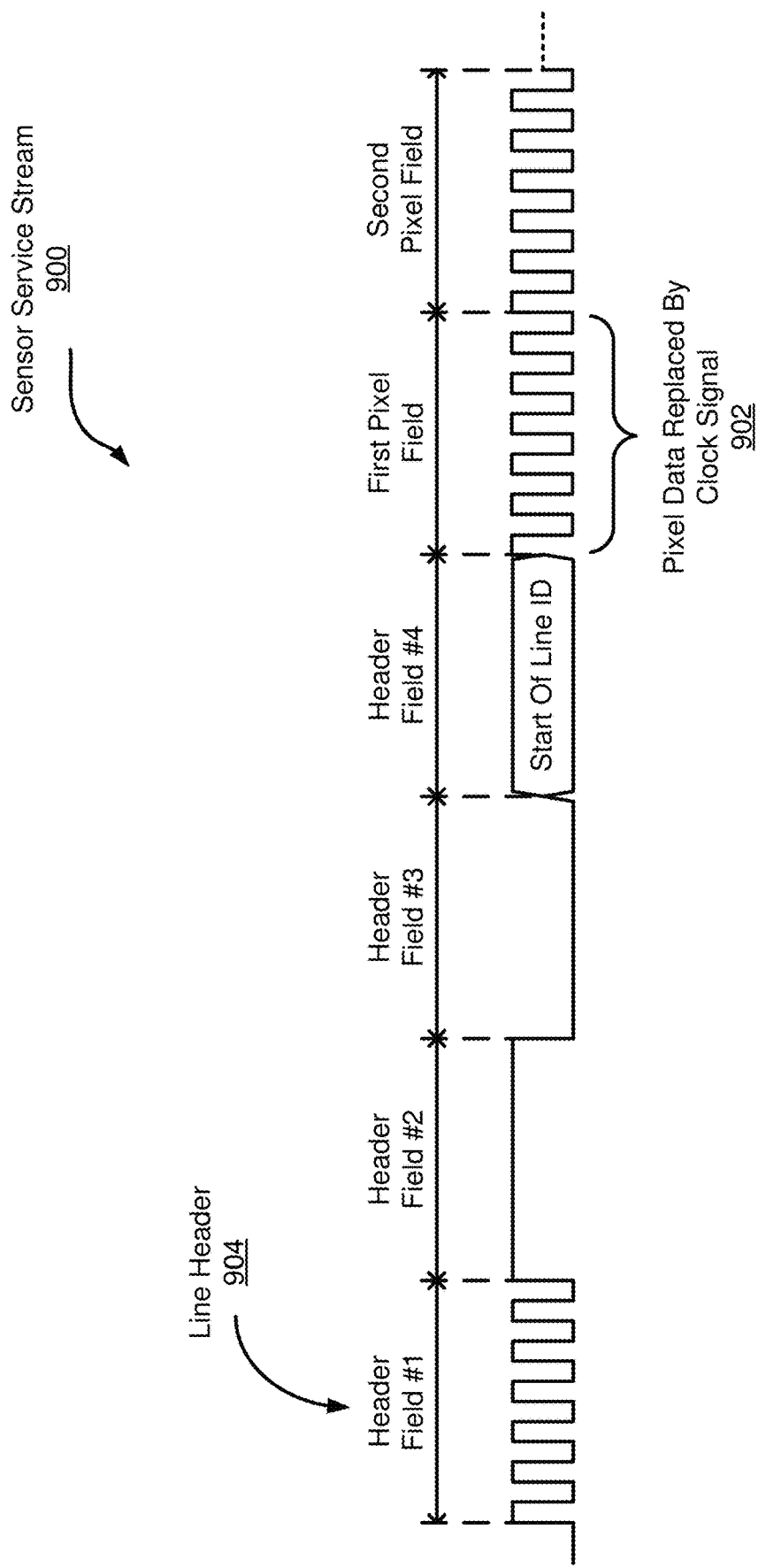
FIG. 9 is a schematic diagram of a sensor service stream that includes a clock-like signal inserted in the output data stream of a pixel array.

FIG. 9 is a schematic diagram of a sensor service stream 900. The sensor service stream 900 includes a clock-like signal inserted in the output data stream of the pixel array at 902. In traditional systems, the clock-like signal would normally be included with pixel data in a cock recovery lin. As shown in FIG. 9, a line header 904 is defined for the camera system to differentiate between clock recovery lines and pixel data lines. In an embodiment, the number of clock recovery lines is adjustable by way of a register setting.

Figure 10:
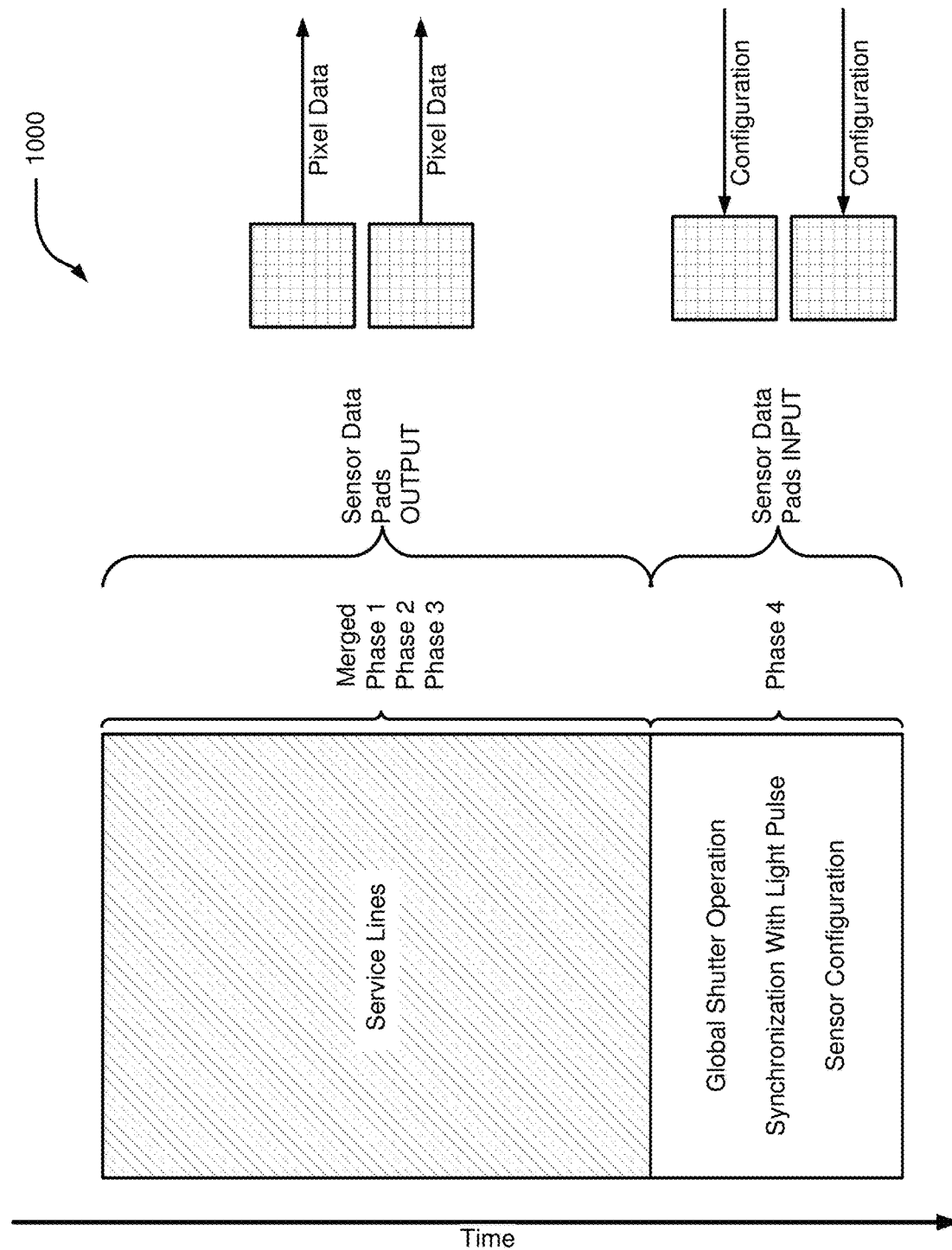
FIG. 10 is a schematic diagram of a clock training sequence that may be deployed when the phase lock loop voltage drifts significantly far from the lock voltage.

FIG. 10 is a schematic diagram of a clock training sequence 1000 of an image sensor. The clock training sequence 1000 may be deployed when the phase lock loop (PLL) voltage drifts significantly far from the lock voltage. This may be particularly common at startup of the image sensor. In the clock training sequence 1000, each of phase 1, phase 2, and phase 3 from the regular operation sequence 800 is merged to form a continuous period of clock training.

The merged phase 1, phase 2, and phase 3 is a service line period. During the merged phase, information is issued from the image sensor. The information does not include signal samples from physical pixels of the pixel array and instead includes data pertaining to synchronization of the image sensor chip with the camera system. The synchronization data can be used for data locking.

During phase 4, information is received by the image sensor. Phase 4 may be referred to as the configuration phase. The duration of phase 4 may be less than about 5-10 milliseconds. This short duration allows for a limited number of clock recovery lines. Therefore, the number of transitions available to re-lock the system may be correspondingly low. In some implementations, this will not cause an issue because the phase lock loop (PLL) voltage of the camera unit Clock Data Recovery (CDR) does not have time to drift far from the lock voltage during phase 4. In the event the phase lock loop voltage drifts significantly far from the lock voltage, the receiver may need a significantly greater number of transitions. In this instance, the clock training sequence 1000 may be used such that phases 1, 2, and 3 are merged to be a continuous clock training phase as shown in FIG. 10. Once the camera unit CDR has locked, the image sensor may resume normal operation as illustrated in the regular operation sequence 800 in FIG. 8. During the regular operation sequence 800, phase 1 may provide smaller adjustments needed for re-locking the camera unit CDR. Therefore, the CDR specification regarding the minimal number of transitions to lock or re-lock may be taken care by combining the clock training sequence 100 and the regular operation sequence 800.

Figure 11:
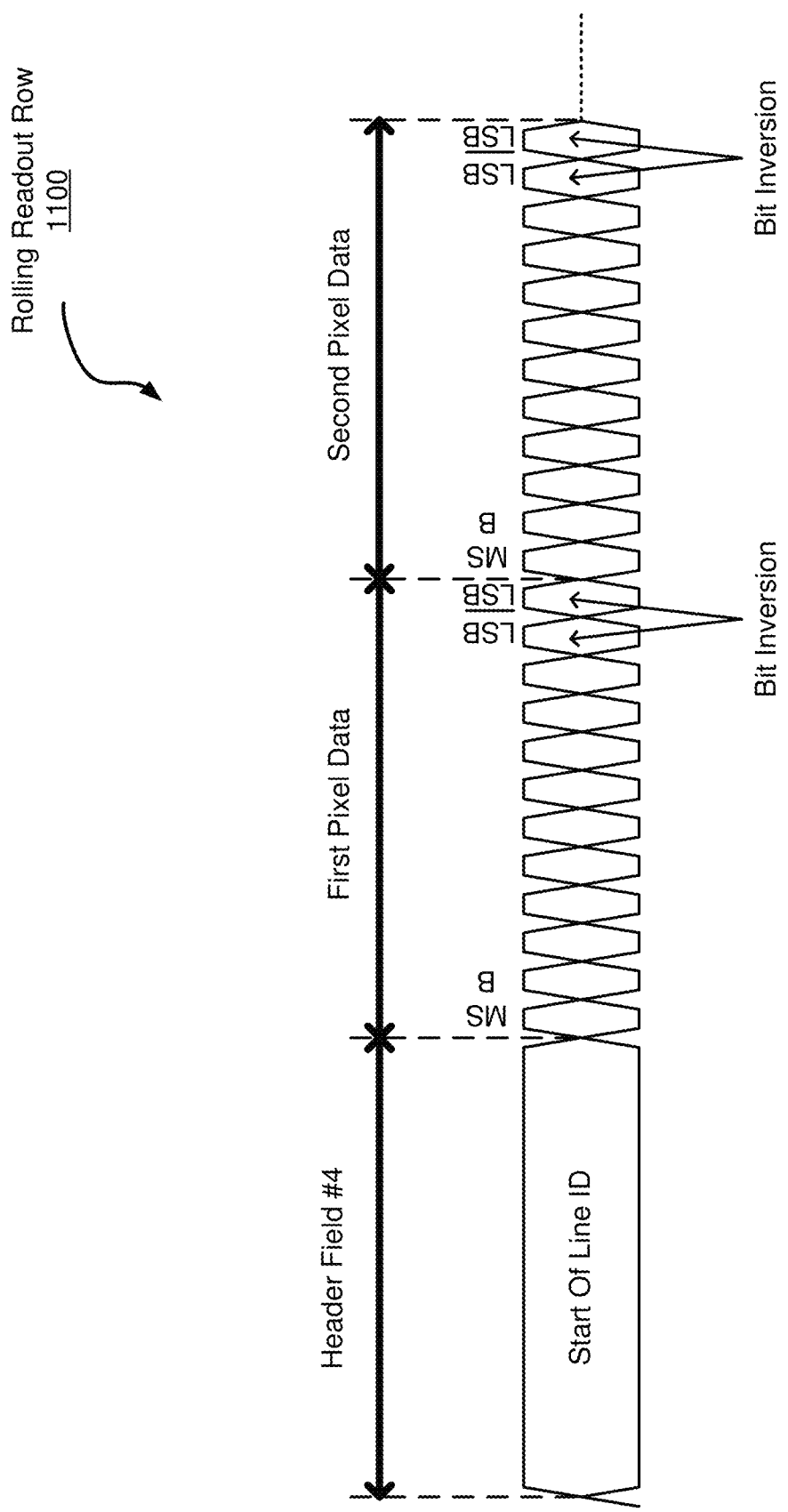
FIG. 11 is a schematic diagram of a rolling readout row used to address the CDR specification concerned with the maximal number of bits between transitions to ensure the CDR does not lose its lock.

FIG. 11 is a schematic diagram of a rolling readout row 1100. The rolling readout row 1100 is used to address the CDR specification concerned with the maximal number of bits between transitions to ensure the CDR does not lose its lock. The rolling readout row 1100 may be based on special encoding of pixel data captured by the pixel array of the image sensor.

In FIG. 11, the actual pixel data values may be 11 bits with the most significant bits (MSB) transmitted first and the least significant bits (LSB) transmitted last. A twelfth bit may be added to each pixel's data. The twelfth bit is an inverted version of the eleventh bit, which is the least significant true bit. This results in an encoding with very little overhead. A high transition rate may be obtained during transmission of pixel data, thereby avoiding any possibility of the camera unit CDR becoming unlocked.

Figure 12B:
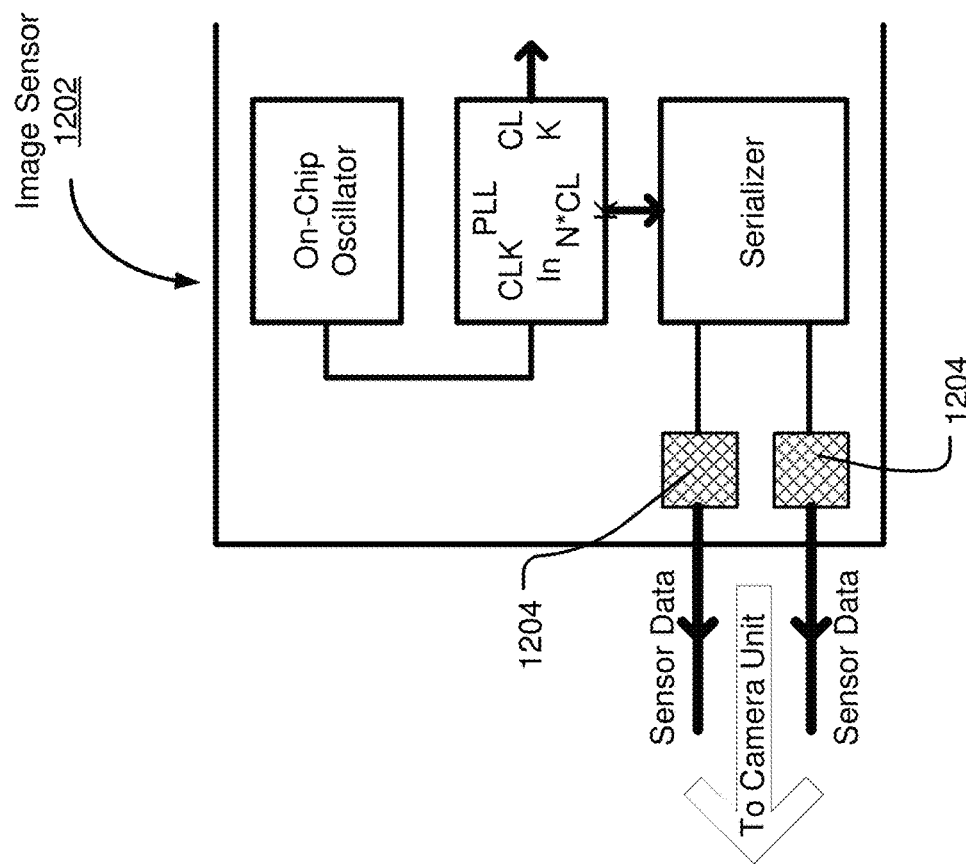
FIG. 12B is a schematic diagram of a conventional method for generating a clock signal that deploys an on-chip oscillator rather than an off-chip oscillator.
Figure 12A:
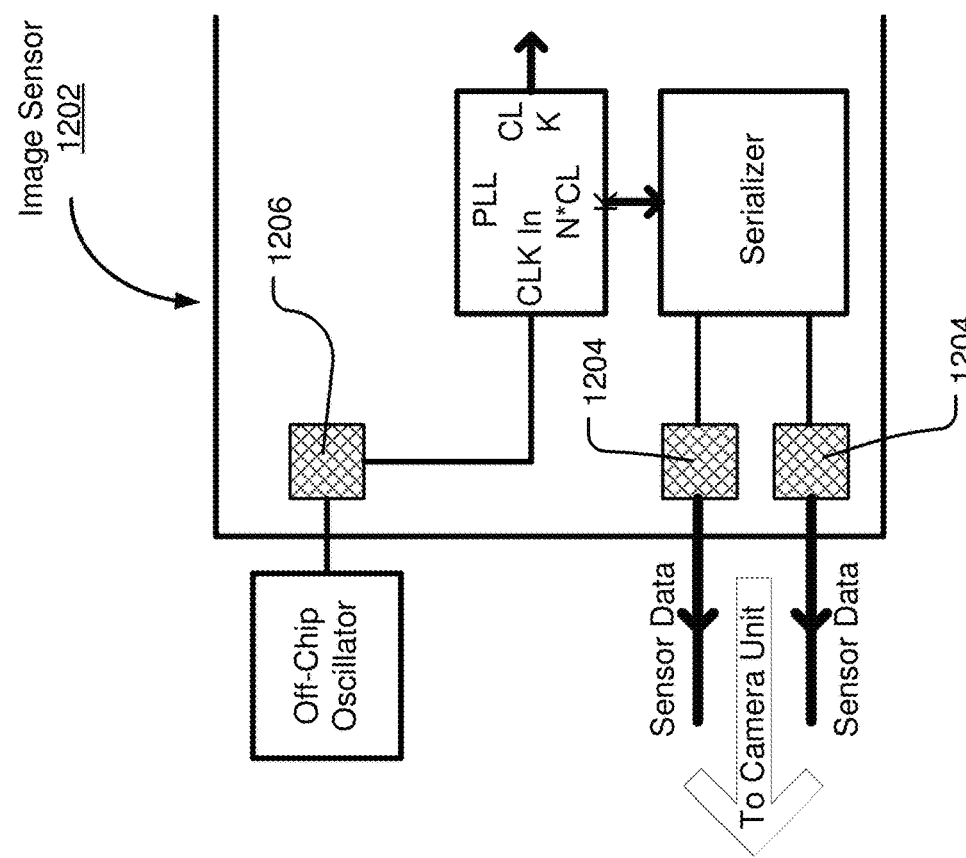
FIG. 12A is a schematic diagram of a conventional method for generating a clock signal wherein an image sensor communicates with an off-chip oscillator.

FIGS. 12A and 12B illustrate schematic diagrams of two conventional methods for generating a clock signal for an image sensor 1202. In the implementation shown in FIG. 12A, the image sensor 1202 communicates with an off-chip oscillator. The off-chip oscillator may be a crystal oscillator and a phase lock loop (PLL) circuit. The implementation shown in FIG. 12A leads to precise results bud adds the burden of an additional pad 1206 and an active component. The active component may require low speed control programming that further increases the conductor count. This may be a disadvantage at the distal tip of an endoscope where space is limited.

In the implementation shown in FIG. 12B, clock generation is executed using an on-chip oscillator rather than the off-chip oscillator shown in FIG. 12A. The implementation shown in FIG. 12B provides an advantageous result in terms of pad 1204 conductor counts. However, such circuits may be inconsistent and exhibit significant variability from chip to chip. Such circuits are often temperature dependent and can be sensitive to any change in temperature. These drawbacks prevent use in applications like video where the framerates needs to be ultra-precise.

The systems, methods, and devices disclosed herein provide means for an on-chip precise clock without additional external components. One benefit of this embodiment is that no additional pads or conductors are required because existing sensor data output pads and low speed control programming pads are repurposed as an on-chip clock.

Figure 13:
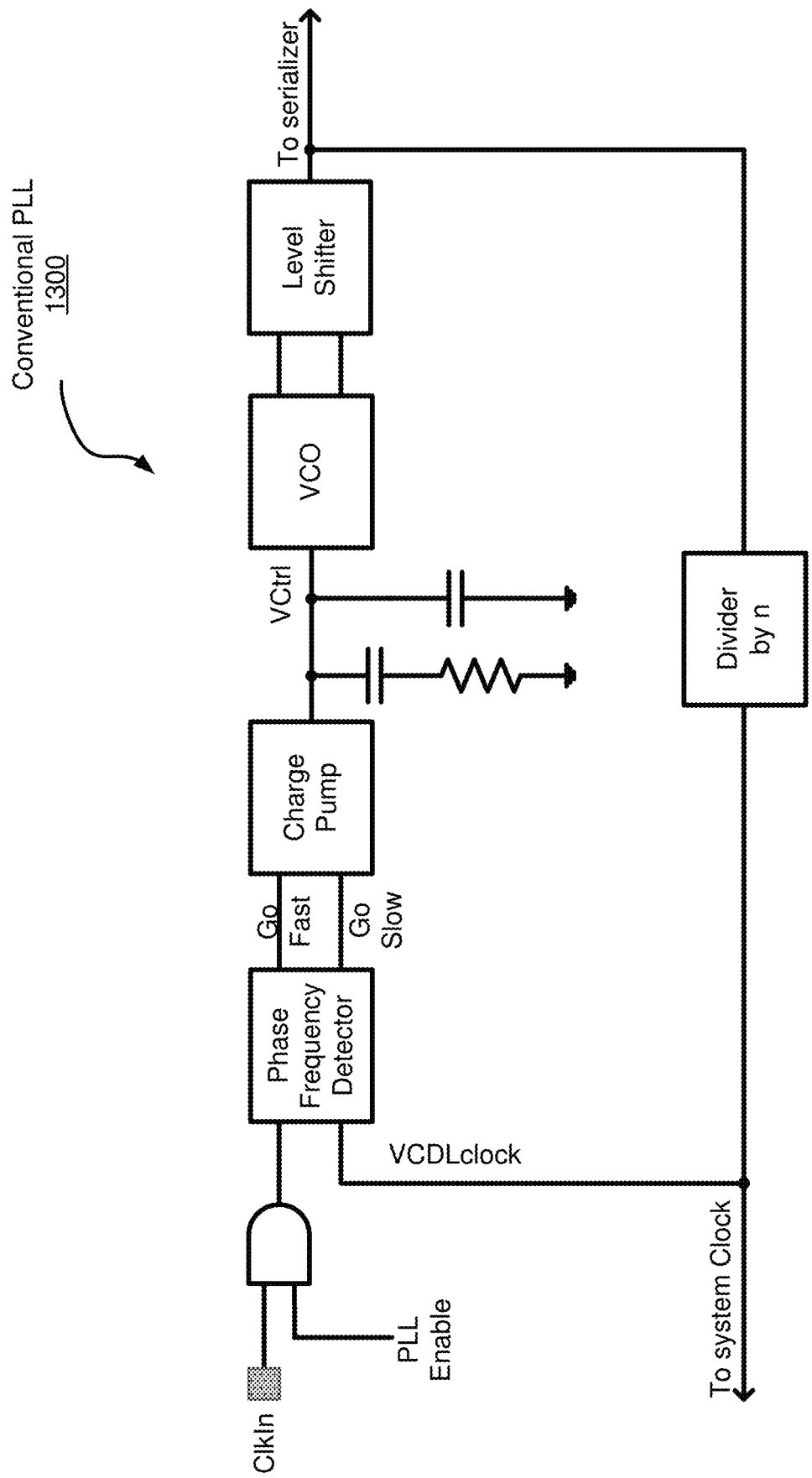
FIG. 13 is a circuit diagram of a conventional phase lock loop.

FIG. 13 is a circuit diagram of a conventional phase lock loop (PLL) 1300. The voltage-controlled delay line (VCDL) clock is compared to the incoming clock. The frequency detector up-pushes and/or down-pushes are issued to the external voltage-controlled oscillator (VCO) depending on the frequency detector comparison result. The conventional phase lock loop 1300 may dynamically react and adjust to ensure the VCDL clock matches the input clock.

The systems, methods, and devices disclosed herein created a phase lock loop that overlaps between the image sensor and the camera unit. This leverages the communication protocol that already exists between the image sensor and the camera unit. In an embodiment, the frequency detector is moved from the phase lock loop to the camera unit. The input of the frequency detector can be attached to the precise clock provided by the camera unit oscillator. The camera unit oscillator does not increase sensor pad count because it is in the camera unit. In an embodiment, digital feed-forward and feedback nodes in the phase lock loop may be selected and matches to the feed-forward system node and the feedback system node. The feed-forward system node is low speed control programming from the camera unit to the image sensor. The feedback system node is pixel data output from the image sensor to the camera unit.

Figure 14:
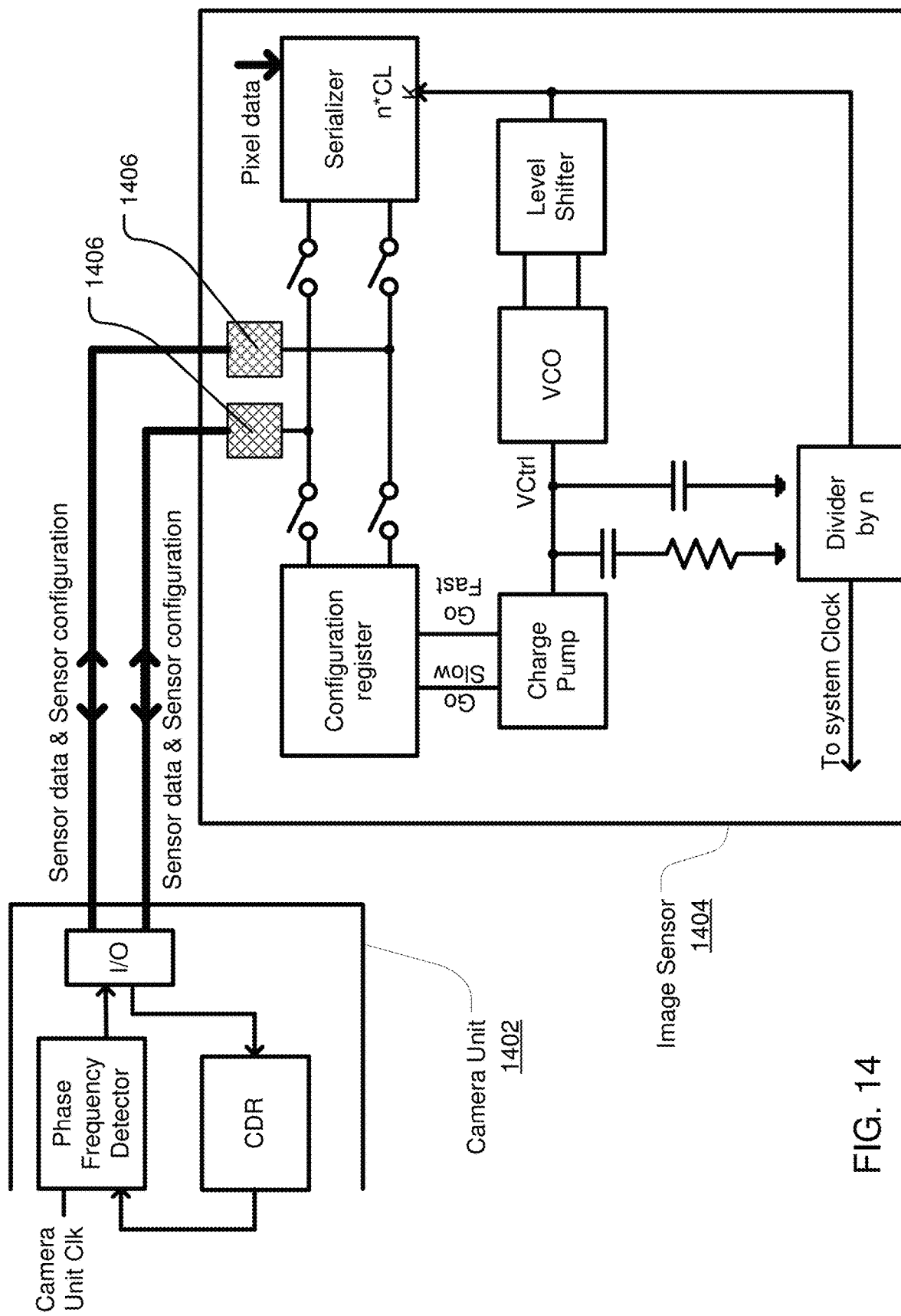
FIG. 14 is a circuit diagram for clock management and data sequencing between a camera unit and an image sensor.

FIG. 14 is a circuit diagram illustrating clock management and data sequencing between a camera unit 1402 and an image sensor 1404. In an embodiment, the image sensor 1404 is a complementary metal oxide semiconductor (CMOS) sensor. In an embodiment, the feed-forward node is the go-fast go-flow signal and is updated using the sensor low speed control programming. The feedback node may be chosen to be the multiplied clock prior to the divider by n. This multiplied frequency may be used to serialize the pixel data and may be decoded by the CDR in the camera unit. The result can then be fed bac to the frequency detector. Such an embodiment does not increase the pad 1406 count or the conductor count.

Figure 15:
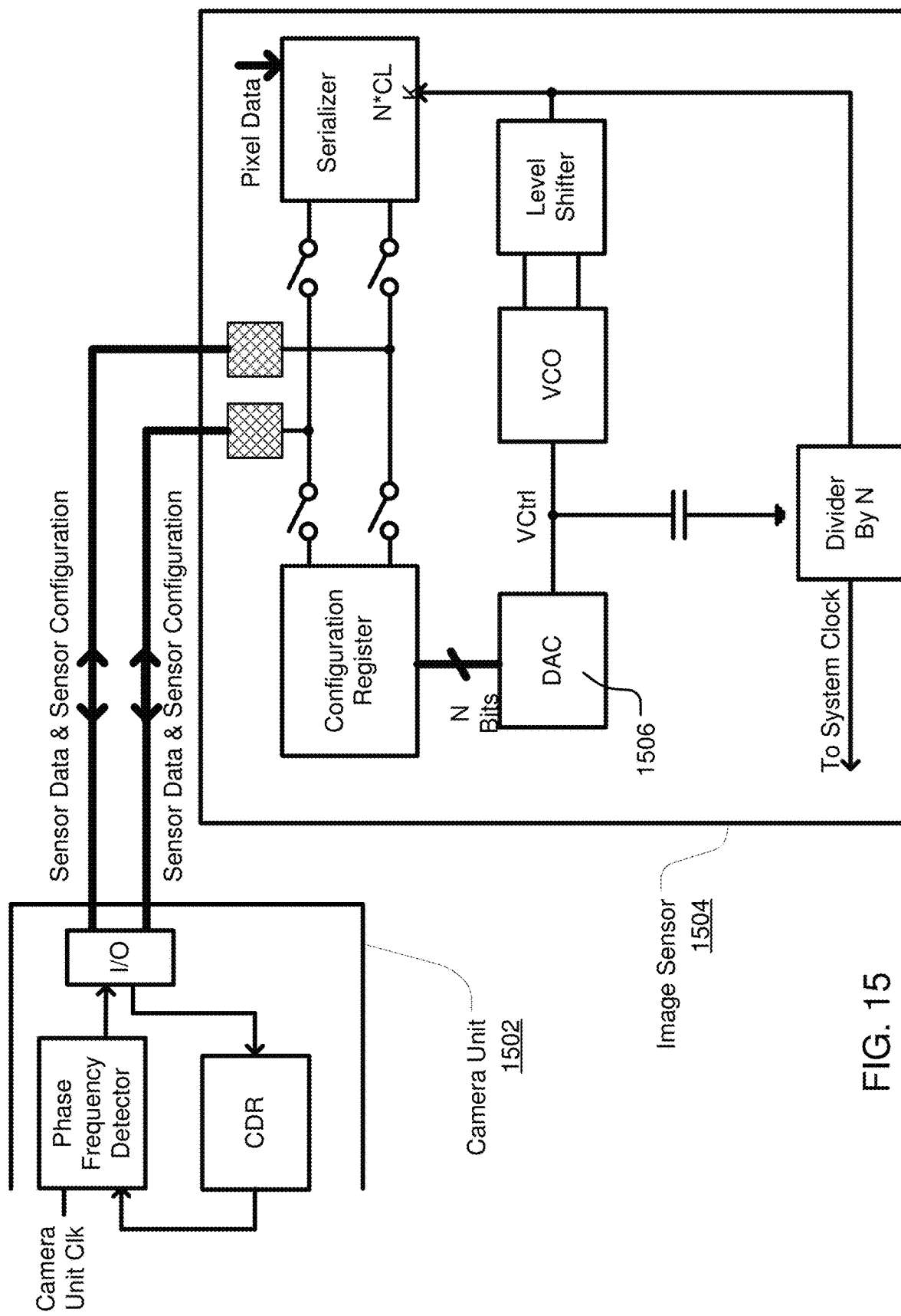
FIG. 15 is a circuit diagram for clock management and data sequencing between a camera unit and an image sensor.

FIG. 15 is a circuit diagram for clock management and data sequencing between a camera unit 1502 and an image sensor 1504. In the embodiment illustrated in FIG. 15, a digital to analog converter (DAC) 1506 is used instead of a charge pump. When the DAC 1506 is implemented, the low speed control may program a configuration register. This is in contrast with the push-up/push-down model implemented with a charge pump.

Figure 16:
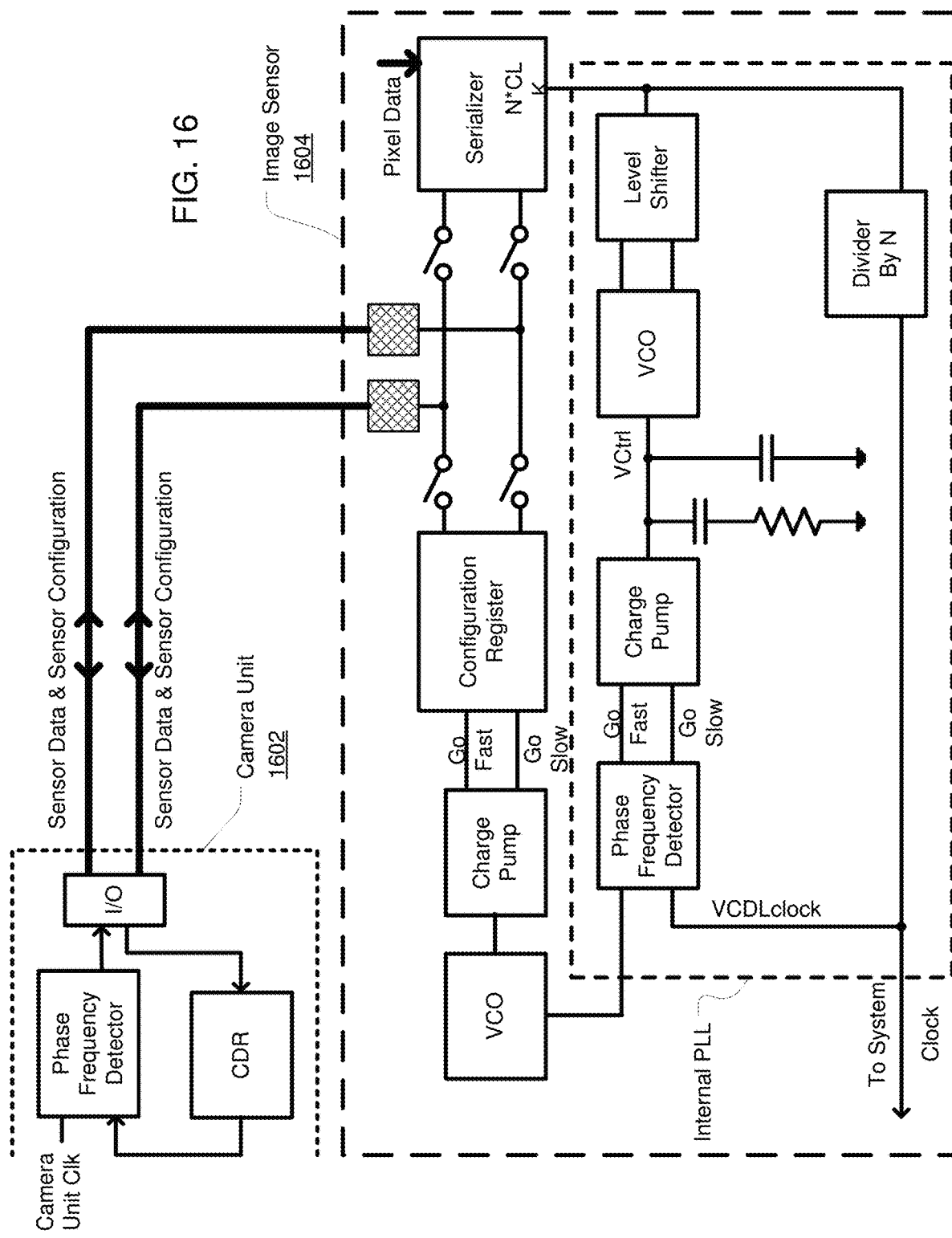
FIG. 16 is a circuit diagram for clock management and data sequencing between a camera unit and an image sensor.

FIG. 16 is a circuit diagram for clock management and data sequencing between a camera unit 1602 and an image sensor 1604 without segmenting the on-chip phase lock loop. The embodiment illustrated in FIG. 16 is an equivalent circuit where the internal phase lock loop remains unchanged and the clock input pad is removed. The input clock signal is provided by a clock generator distributed circuit equivalent to that of FIG. 14.

Figure 17:
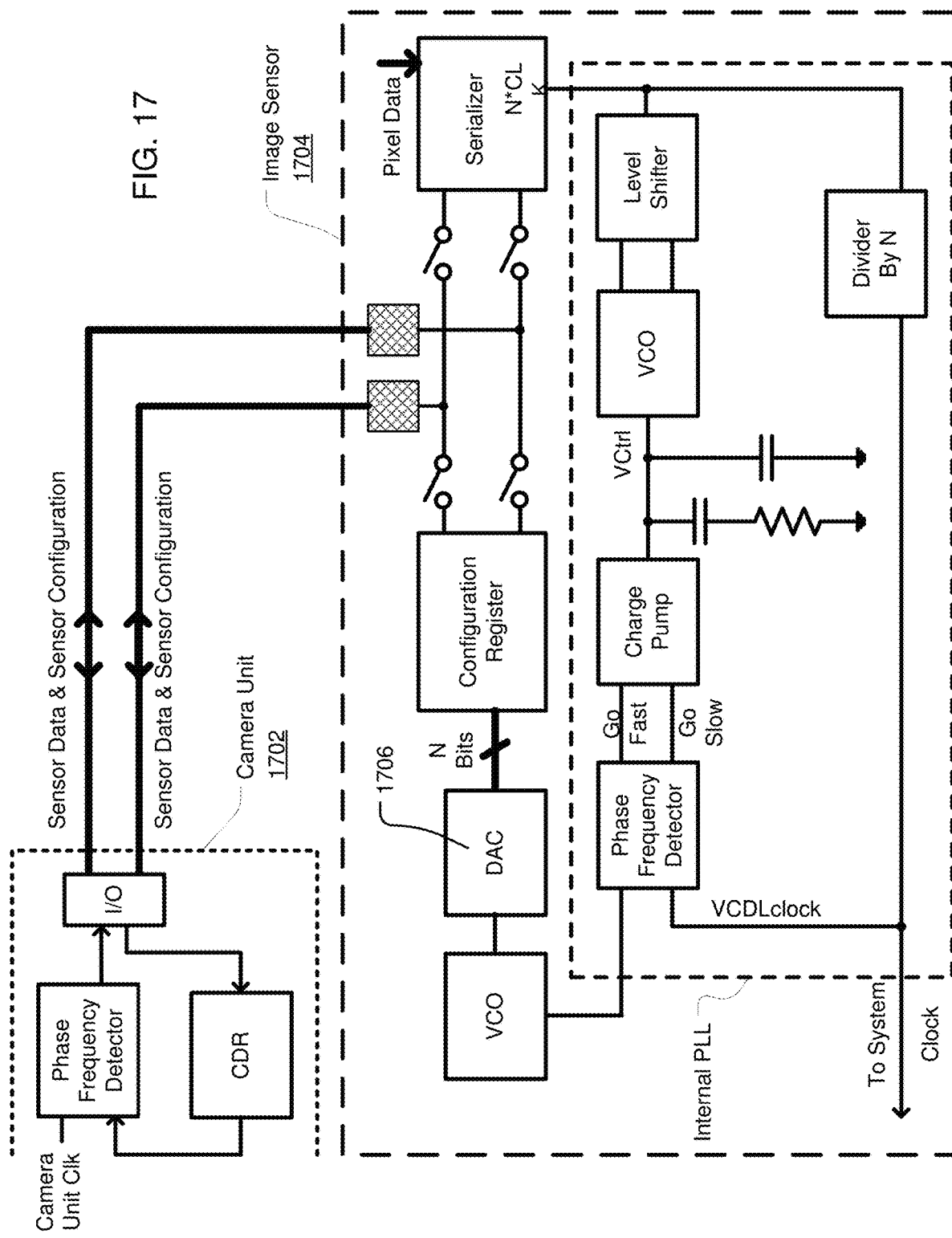
FIG. 17 is a circuit diagram for clock management and data sequencing between a camera unit and an image sensor.

FIG. 17 is a circuit diagram for clock management and data sequencing between a camera unit 1702 and an image sensor 1704. In the embodiment illustrated in FIG. 17, the image sensor 1704 uses a digital to analog converter (DAC) 1706 rather than a charge pump.

Figure 18:
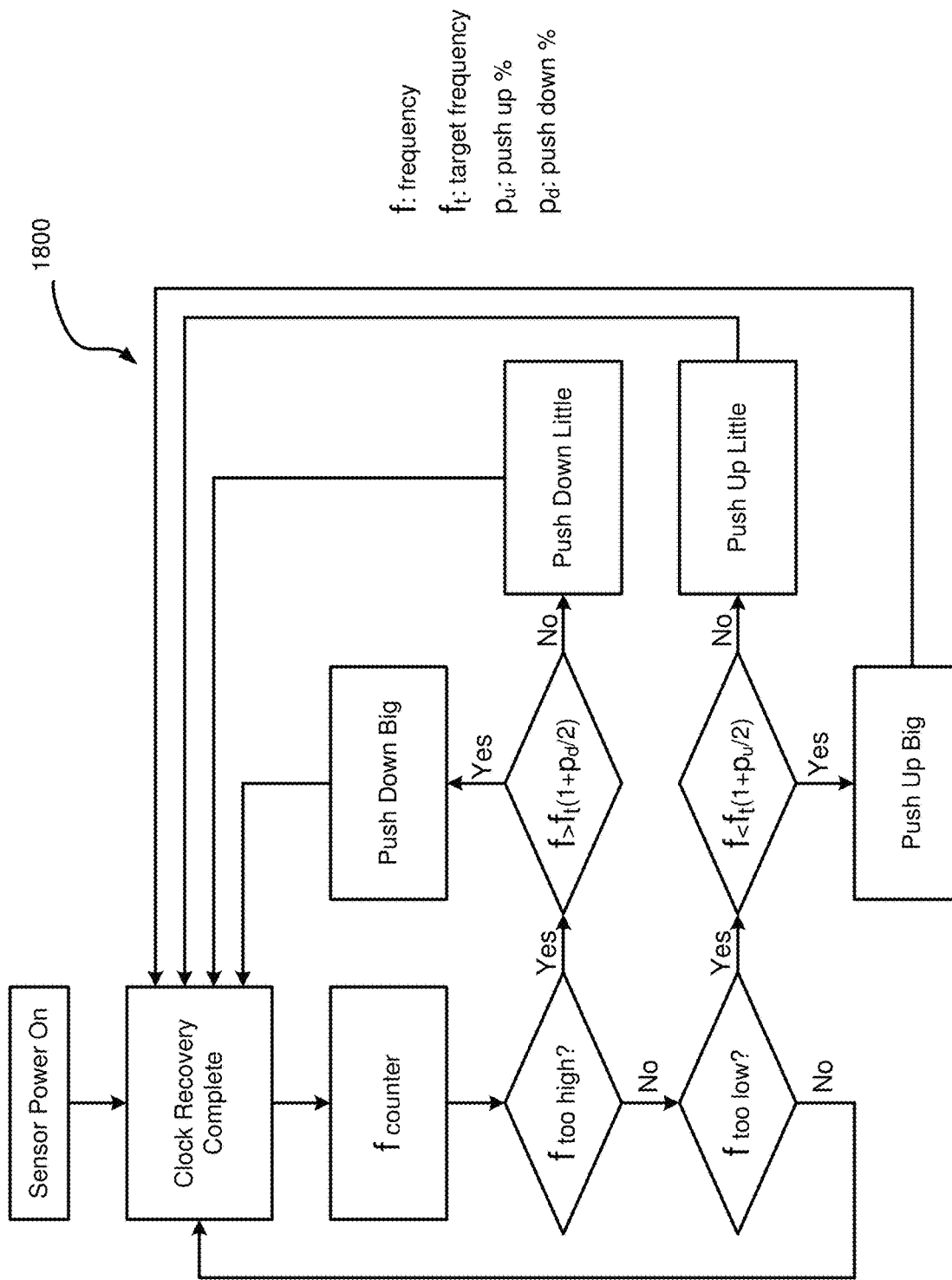
FIG. 18 is a schematic diagram of a process flow that may be implemented by a camera unit implemented in a charge pump system.

FIG. 18 is a schematic diagram of a process flow 1800 for an algorithm that may reside in the camera unit. The process flow 1800 may be implemented in a charge pump system. The process flow 1800 includes powering on the image sensor and performing clock recovery. The process flow 1800 includes performing a frequency counter and determining whether the frequency is too high or too low. The process flow 1800 includes performing push-ups and push-downs in response to calculations as illustrated in FIG. 18.

FIG. 19 is a table listing signals and parameters that may be used by the camera unit for the process flow 1800 illustrated in FIG. 18. An example implementation of the process flow 1800 algorithm includes the following. The R_CLK may be compared to the target frequency using REF_CLK as the method or mode of comparison. If R_CLK is too low, then PUSH UP may be asserted. If R_CLK is too high, then PUSH DOWN may be asserted. The BIG_LITTLE output may be used based on how far R_CLK is from the target frequency. As an example, if a big push represents a 5% change and a little push represents a 1% change in frequency then if R_CLK is lower than target frequency minus 3%, the block may issue a PUSH UP BIG command. The next time the R_CLK is measured it will be approximately 2% greater than the target and so the block may issue a PUSH DOWN LITTLE command.

The method of comparing the R_CLK to the target frequency may be as follows. In an example, if the REF_CLK is 27 MHz, the target is 40 MHz and the R_CLK is 38 MHz, then the block may count the number of R_CLK transitions over 1 ms (or 27,000 transitions of REF_CLK). It may compare its counter value, now 38,000 to the desired target of 40,000 and issue a PUSH UP BIG command assuming the BIG and LITTLE thresholds are 5% and 1%.

Figure 20:
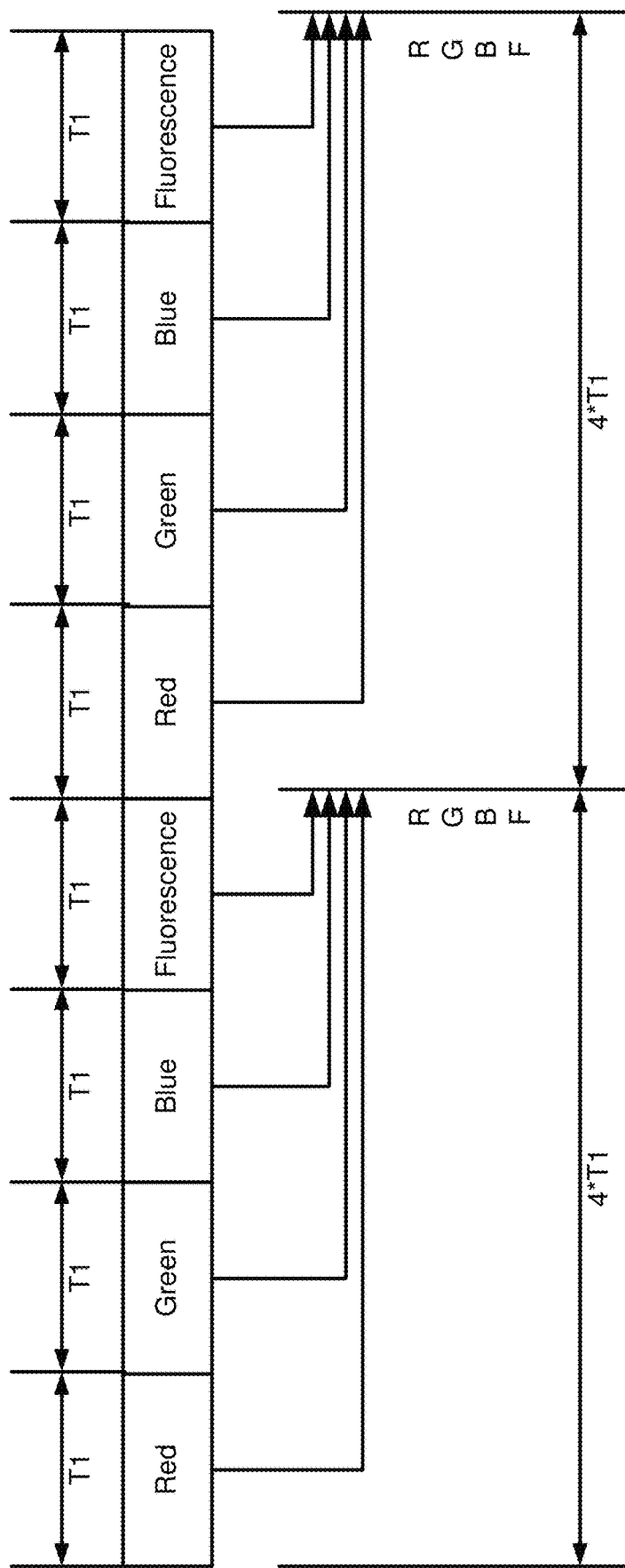
FIG. 20 is a schematic diagram of a pattern reconstruction process for generating an RGB image with fluorescence data overlaid thereon by pulsing partitioned spectrums of light.

FIG. 20 is a schematic diagram of a pattern reconstruction process. The example pattern illustrated in FIG. 20 includes Red, Green, Blue, and Fluorescence pulses of light that each last a duration of T1. In various embodiments, the pulses of light may be of the same duration or of differing durations. The Red, Green, Blue, and Fluorescence exposure frames are combined to generate an RGB image with fluorescence data overlaid thereon. A single image frame comprising a red exposure frame, a green exposure frame, a blue exposure frame, and a fluorescence exposure frame requires a time period of 4*T1 to be generated. The time durations shown in FIG. 20 are illustrative only and may vary for different implementations. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

In an embodiment, the dynamic range of the system is increased by varying the pixel sensitivities of pixels within the pixel array of the image sensor. Some pixels may sense reflected electromagnetic radiation at a first sensitivity level, other pixels may sense reflected electromagnetic radiation at a second sensitivity level, and so forth. The different pixel sensitivities may be combined to increase the dynamic range provided by the pixel configuration of the image sensor. In an embodiment, adjacent pixels are set at different sensitivities such that each cycle includes data produced by pixels that are more and less sensitive with respect to each other. The dynamic range is increased when a plurality of sensitivities are recorded in a single cycle of the pixel array. In an embodiment, wide dynamic range can be achieved by having multiple global TX, each TX firing only on a different set of pixels. For example, in global mode, a global TX1 signal is firing a set 1 of pixels, a global TX2 signal is firing a set 2 of pixel, a global TXn signal is firing a set n of pixels, and so forth.

Figure 21A:
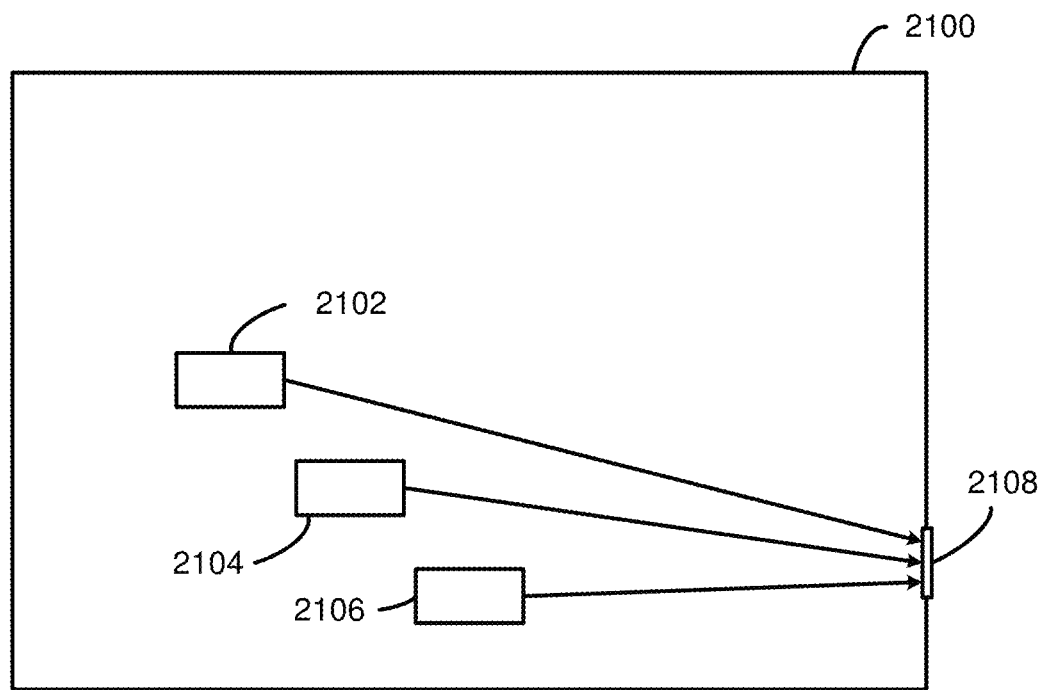
FIGS. 21A-21C illustrate a light source having a plurality of emitters.
Figure 21B:
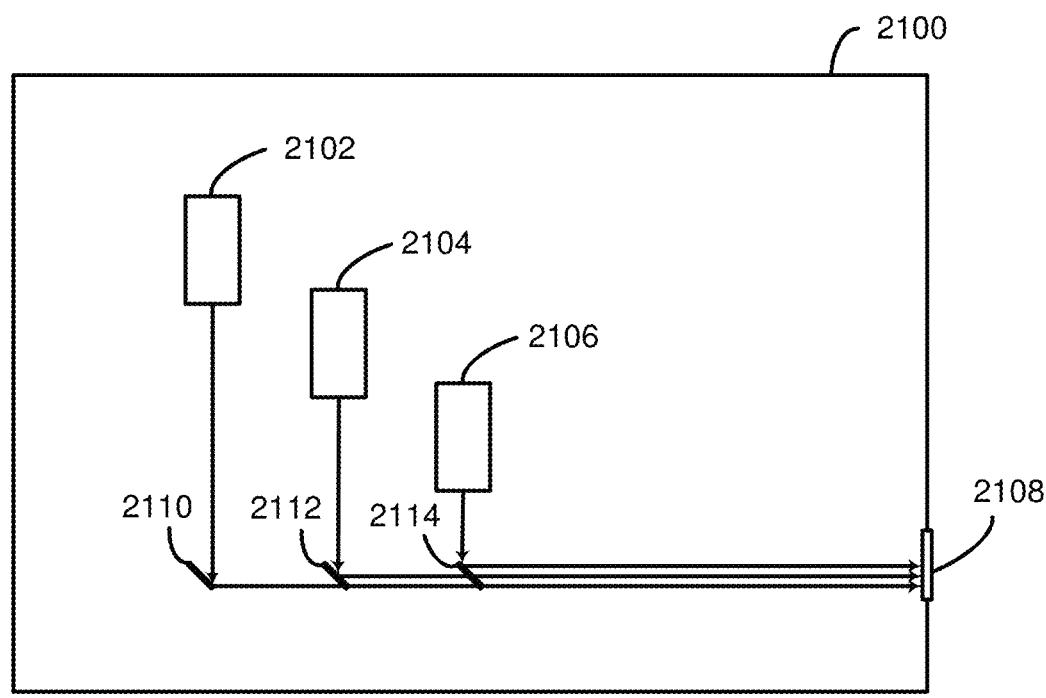
Figure 21C:
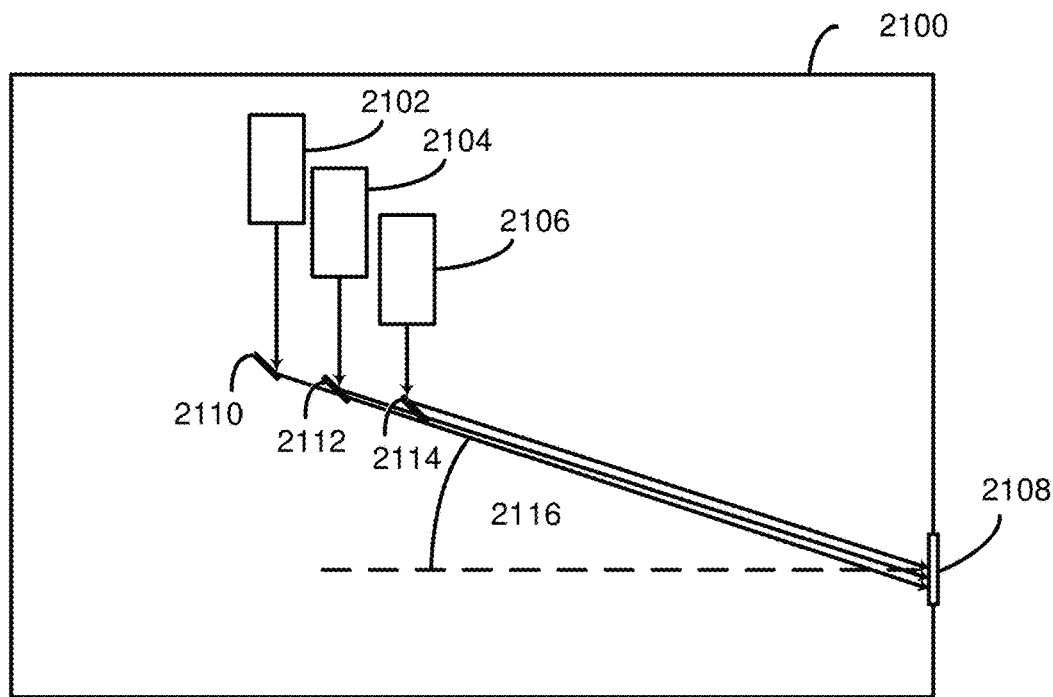

FIGS. 21A-21C each illustrate a light source 2100 having a plurality of emitters. The emitters include a first emitter 2102, a second emitter 2104, and a third emitter 2106. Additional emitters may be included, as discussed further below. The emitters 2102, 2104, and 2106 may include one or more laser emitters that emit light having different wavelengths. For example, the first emitter 2102 may emit a wavelength that is consistent with a blue laser, the second emitter 2104 may emit a wavelength that is consistent with a green laser, and the third emitter 2106 may emit a wavelength that is consistent with a red laser. For example, the first emitter 2102 may include one or more blue lasers, the second emitter 2104 may include one or more green lasers, and the third emitter 2106 may include one or more red lasers. The emitters 2102, 2104, 2106 emit laser beams toward a collection region 2108, which may be the location of a waveguide, lens, or other optical component for collecting and/or providing light to a waveguide, such as the jumper waveguide 206 or lumen waveguide 210 of FIG. 2.

In an implementation, the emitters 2102, 2104, and 2106 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 2102, 2104, and 2106 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 2102, 2104, and 2106 emit a laser mapping pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 2102, 2104, and 2106 may emit a laser mapping pattern such that a laser mapping pattern is projected on to each tool individually. In such an embodiment, the laser mapping data for each of the tools can be analyzed to identify distances between the tools and other objects in the scene.

In the embodiment of FIG. 21B, the emitters 2102, 2104, 2106 each deliver laser light to the collection region 2108 at different angles. The variation in angle can lead to variations where electromagnetic energy is located in an output waveguide. For example, if the light passes immediately into a fiber bundle (glass or plastic) at the collection region 2108, the varying angles may cause different amounts of light to enter different fibers. For example, the angle may result in intensity variations across the collection region 2108. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 2102, 2104, 2106 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 2108 is represented as a physical component in FIG. 21A, the collection region 2108 may simply be a region where light from the emitters 2102, 2104, and 2106 is delivered. In some cases, the collection region 2108 may include an optical component such as a diffuser, mixing rod, lens, or any other intervening optical component between the emitters 2102, 2104, 2106 and an output waveguide.

FIG. 21C illustrates an embodiment of a light source 2100 with emitters 2102, 2104, 2106 that provide light to the collection region 2108 at the same or substantially same angle. The light is provided at an angle substantially perpendicular to the collection region 2108. The light source 2100 includes a plurality of dichroic mirrors including a first dichroic mirror 2110, a second dichroic mirror 2112, and a third dichroic mirror 2114. The dichroic mirrors 2110, 2112, 2114 include mirrors that reflect a first wavelength of light but transmit (or are transparent to) a second wavelength of light. For example, the third dichroic mirror 2114 may reflect blue laser light provided by the third emitter, while being transparent to the red and green light provided by the first emitter 2102 and the second emitter 2104, respectively. The second dichroic mirror 2112 may be transparent to red light from the first emitter 2102, but reflective to green light from the second emitter 2104. If other colors or wavelengths are included dichroic mirrors may be selected to reflect light corresponding to at least one emitter and be transparent to other emitters. For example, the third dichroic mirror 2114 reflect the light form the third emitter 2106 but is to emitters "behind" it, such as the first emitter 2102 and the second emitter 2104. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 2108 at a substantially same angle.

Because the dichroic mirrors allow other wavelengths to transmit or pass through, each of the wavelengths may arrive at the collection region 2108 from a same angle and/or with the same center or focal point. Providing light from the same angle and/or same focal/center point can significantly improve reception and color mixing at the collection region 2108. For example, a specific fiber may receive the different colors in the same proportions they were transmitted/reflected by the emitters 2102, 2104, 2106 and mirrors 2110, 2112, 2114. Light mixing may be significantly improved at the collection region compared to the embodiment of FIG. 21B. In one embodiment, any optical components discussed herein may be used at the collection region 2108 to collect light prior to providing it to a fiber or fiber bundle.

FIG. 21C illustrates an embodiment of a light source 2100 with emitters 2102, 2104, 2106 that also provide light to the collection region 2108 at the same or substantially same angle. However, the light incident on the collection region 2108 is offset from being perpendicular. Angle 2116 indicates the angle offset from perpendicular. In one embodiment, the laser emitters 2102, 2104, 2106 may have cross sectional intensity profiles that are Gaussian. As discussed previously, improved distribution of light energy between fibers may be accomplished by creating a more flat or top-hat shaped intensity profile. In one embodiment, as the angle 2116 is increased, the intensity across the collection region 2108 approaches a top hat profile. For example, a top-hat profile may be approximated even with a non-flat output beam by increasing the angle 2116 until the profile is sufficiently flat. The top hat profile may also be accomplished using one or more lenses, diffusers, mixing rods, or any other intervening optical component between the emitters 2102, 2104, 2106 and an output waveguide, fiber, or fiber optic bundle.

Figure 22:
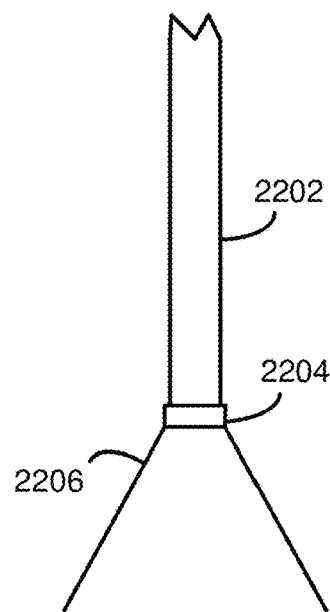
FIG. 22 illustrates a single optical fiber outputting via a diffuser at an output to illuminate a scene in a light deficient environment.

FIG. 22 is a schematic diagram illustrating a single optical fiber 2202 outputting via a diffuser 2204 at an output. In one embodiment, the optical fiber 2202 has a diameter of 500 microns, a numerical aperture of 0.65, and emits a light cone 2206 of about 70 or 80 degrees without a diffuser 2204. With the diffuser 2204, the light cone 2206 may have an angle of about 110 or 120 degrees. The light cone 2206 may be a majority of where all light goes and is evenly distributed. The diffuser 2204 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 21A-21C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 23:
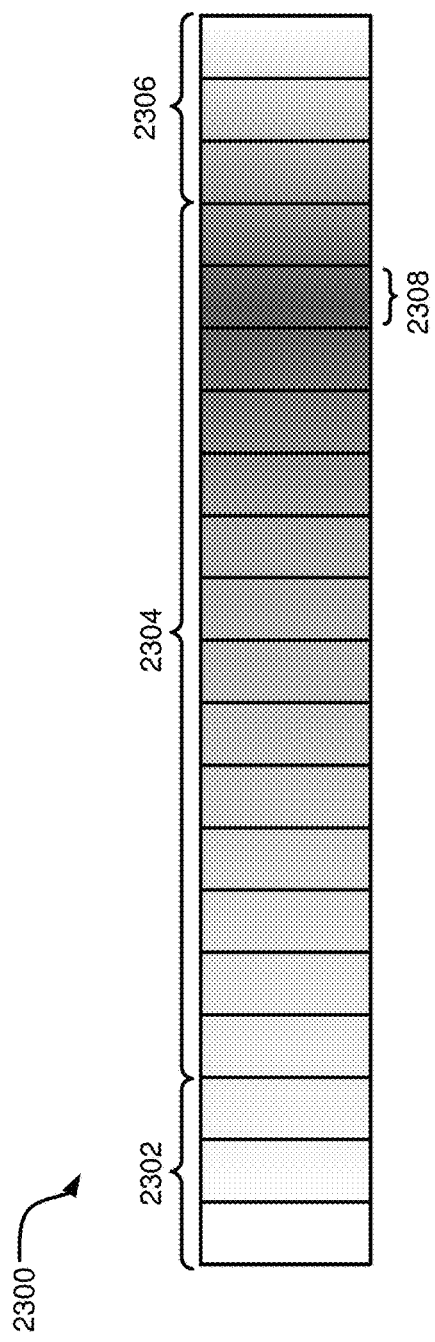
FIG. 23 illustrates a portion of the electromagnetic spectrum divided into a plurality of different sub-spectrums which may be emitted by emitters of a light source in accordance with the principles and teachings of the disclosure.

FIG. 23 illustrates a portion of the electromagnetic spectrum 2300 divided into twenty different sub-spectrums. The number of sub-spectrums is illustrative only. In at least one embodiment, the spectrum 2300 may be divided into hundreds of sub-spectrums, each with a small waveband. The spectrum may extend from the infrared spectrum 2302, through the visible spectrum 2304, and into the ultraviolet spectrum 2306. The sub-spectrums each have a waveband 2308 that covers a portion of the spectrum 2300. Each waveband may be defined by an upper wavelength and a lower wavelength.

Hyperspectral imaging includes imaging information from across the electromagnetic spectrum 2300. A hyperspectral pulse of electromagnetic radiation may include a plurality of sub-pulses spanning one or more portions of the electromagnetic spectrum 2300 or the entirety of the electromagnetic spectrum 2300. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 2300 and may include multiple exposure frames for multiple partitions of the electromagnetic spectrum 2300. In an embodiment, a hyperspectral exposure frame includes multiple hyperspectral exposure frames such that the combined hyperspectral exposure frame comprises data for the entirety of the electromagnetic spectrum 2300.

In one embodiment, at least one emitter (such as a laser emitter) is included in a light source (such as the light sources 202, 2100) for each sub-spectrum to provide complete and contiguous coverage of the whole spectrum 2300. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 24:
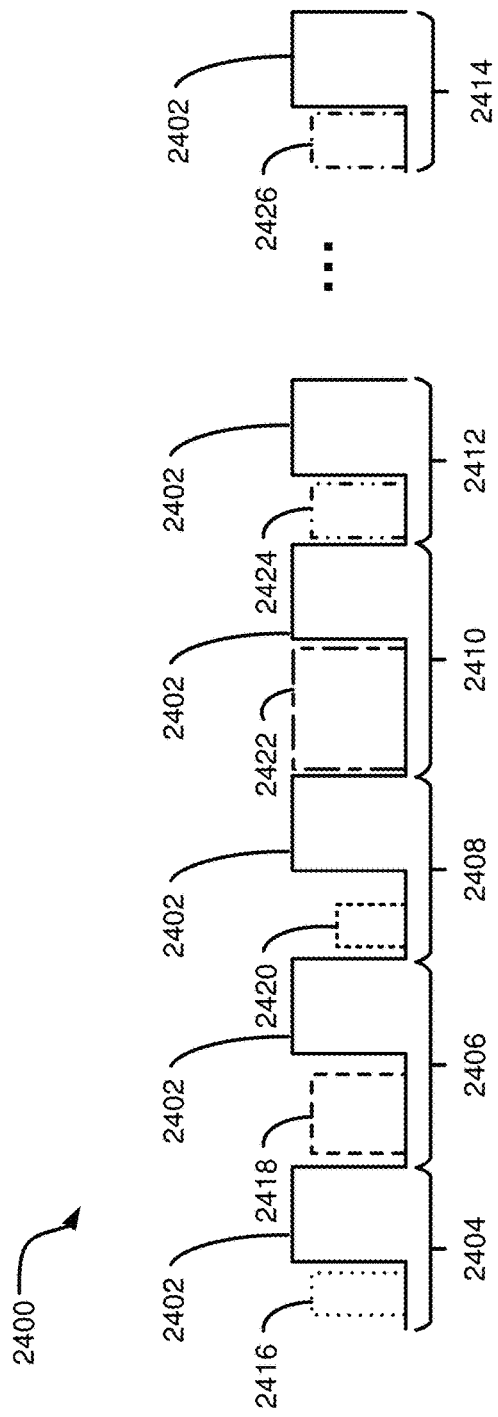
FIG. 24 is a schematic diagram illustrating a timing sequence for emission and readout for generating an image frame comprising a plurality of exposure frames resulting from differing partitions of pulsed light.

FIG. 24 is a schematic diagram illustrating a timing diagram 2400 for emission and readout for generating an image. The solid line represents readout (peaks 2402) and blanking periods (valleys) for capturing a series of exposure frames 2404-2414. The series of exposure frames 2404-2414 may include a repeating series of exposure frames which may be used for generating laser mapping, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser mapping data. The multiple exposure frames are combined to produce the single image frame. In an embodiment, the single image frame is an RGB image with fluorescence imaging data overlaid on the RGB image. The series of exposure frames include a first exposure frame 2404, a second exposure frame 2406, a third exposure frame 2408, a fourth exposure frame 2410, a fifth exposure frame 2412, and an Nth exposure frame 2426.

Additionally, the hyperspectral image data, the fluorescence image data, and the laser mapping data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser mapping data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser mapping data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (2402). Thus, each blanking period and readout results in an exposure frame for a specific spectrum of electromagnetic energy. For example, the first exposure frame 2404 may be generated based on a spectrum of a first one or more pulses 2416, a second exposure frame 2406 may be generated based on a spectrum of a second one or more pulses 2418, a third exposure frame 2408 may be generated based on a spectrum of a third one or more pulses 2420, a fourth exposure frame 2410 may be generated based on a spectrum of a fourth one or more pulses 2422, a fifth exposure frame 2412 may be generated based on a spectrum of a fifth one or more pulses 2424, and an Nth exposure frame 2426 may be generated based on a spectrum of an Nth one or more pulses 2426.

The pulses 2416-2426 may include energy from a single emitter or from a combination of two or more emitters. For example, the spectrum included in a single readout period or within the plurality of exposure frames 2404-2414 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 2416 may include red light, pulse 2418 may include blue light, and pulse 2420 may include green light while the remaining pulses 2422-2426 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 2404-2414 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser mapping pulsing scheme for generating a topology of the scene and calculating dimensions for objects within the scene. The location of the cancerous cells (as identified by the fluorescence imaging data) may be combined with the topology and dimensions information calculated based on the laser mapping data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser mapping pulsing scheme for generating a topology of the scene and calculating dimensions of objects within the scene. The location of the diseased tissue (as identified by the hyperspectral imaging data) may be combined with the topology and dimensions information that is calculated with the laser mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 25:
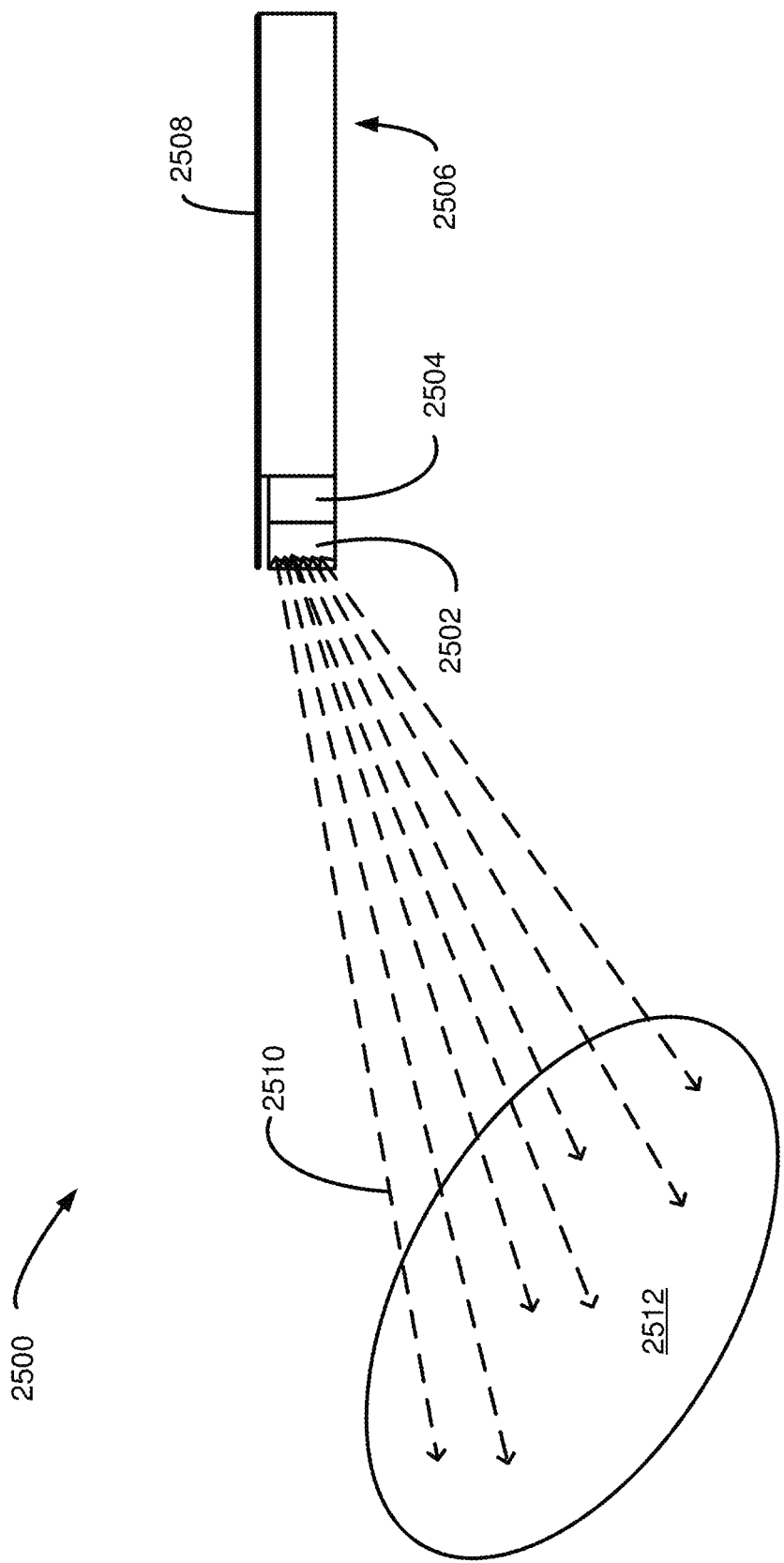
FIG. 25 illustrates an imaging system including a single cut filter for filtering wavelengths of electromagnetic radiation.

FIG. 25 is a schematic diagram of an imaging system 2500 having a single cut filter. The system 2500 includes an endoscope 2506 or other suitable imaging device having a light source 2508 for use in a light deficient environment. The endoscope 2506 includes an image sensor 2504 and a filter 2502 for filtering out unwanted wavelengths of light or other electromagnetic radiation before reaching the image sensor 2504. The light source 2508 transmits light that may illuminate the surface 2512 in a light deficient environment such as a body cavity. The light 2510 is reflected off the surface 2512 and passes through the filter 2502 before hitting the image sensor 2504.

The filter 2502 may be used in an implementation where a fluorescent reagent or dye has been administered. In such an embodiment, the light source 2508 emits the excitation wavelength for fluorescing the fluorescent reagent or dye. Commonly, the relaxation wavelength emitted by the fluorescent reagent or dye will be of a different wavelength than the excitation wavelength. The filter 2502 may be selected to filter out the excitation wavelength and permit only the relaxation wavelength to pass through the filter and be sensed by the image sensor 2504.

In one embodiment, the filter 2502 is configured to filter out an excitation wavelength of electromagnetic radiation that causes a reagent or dye to fluoresce such that only the expected relaxation wavelength of the fluoresced reagent or dye is permitted to pass through the filter 2502 and reach the image sensor 2504. In an embodiment, the filter 2502 filters out at least a fluorescent reagent excitation wavelength between 770 nm and 790 nm. In an embodiment, the filter 2502 filters out at least a fluorescent reagent excitation wavelength between 795 nm and 815 nm. In an embodiment, the filter 2502 filters out at least a fluorescent reagent excitation wavelength between 770 nm and 790 nm and between 795 nm and 815 nm. In these embodiments, the filter 2502 filters out the excitation wavelength of the reagent and permits only the relaxation wavelength of the fluoresced reagent to be read by the image sensor 2504. The image sensor 2504 may be a wavelength-agnostic image sensor and the filter 2502 may be configured to permit the image sensor 2504 to only receive the relaxation wavelength of the fluoresced reagent and not receive the emitted excitation wavelength for the reagent. The data determined by the image sensor 2504 may then indicate a presence of a critical body structure, tissue, biological process, or chemical process as determined by a location of the reagent or dye.

The filter 2502 may further be used in an implementation where a fluorescent reagent or dye has not been administered. The filter 2502 may be selected to permit wavelengths corresponding to a desired spectral response to pass through and be read by the image sensor 2504. The image sensor 2504 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 2504, may indicate the presence of a certain body tissue or structure, a certain condition, a certain chemical process, and so forth.

Figure 26:
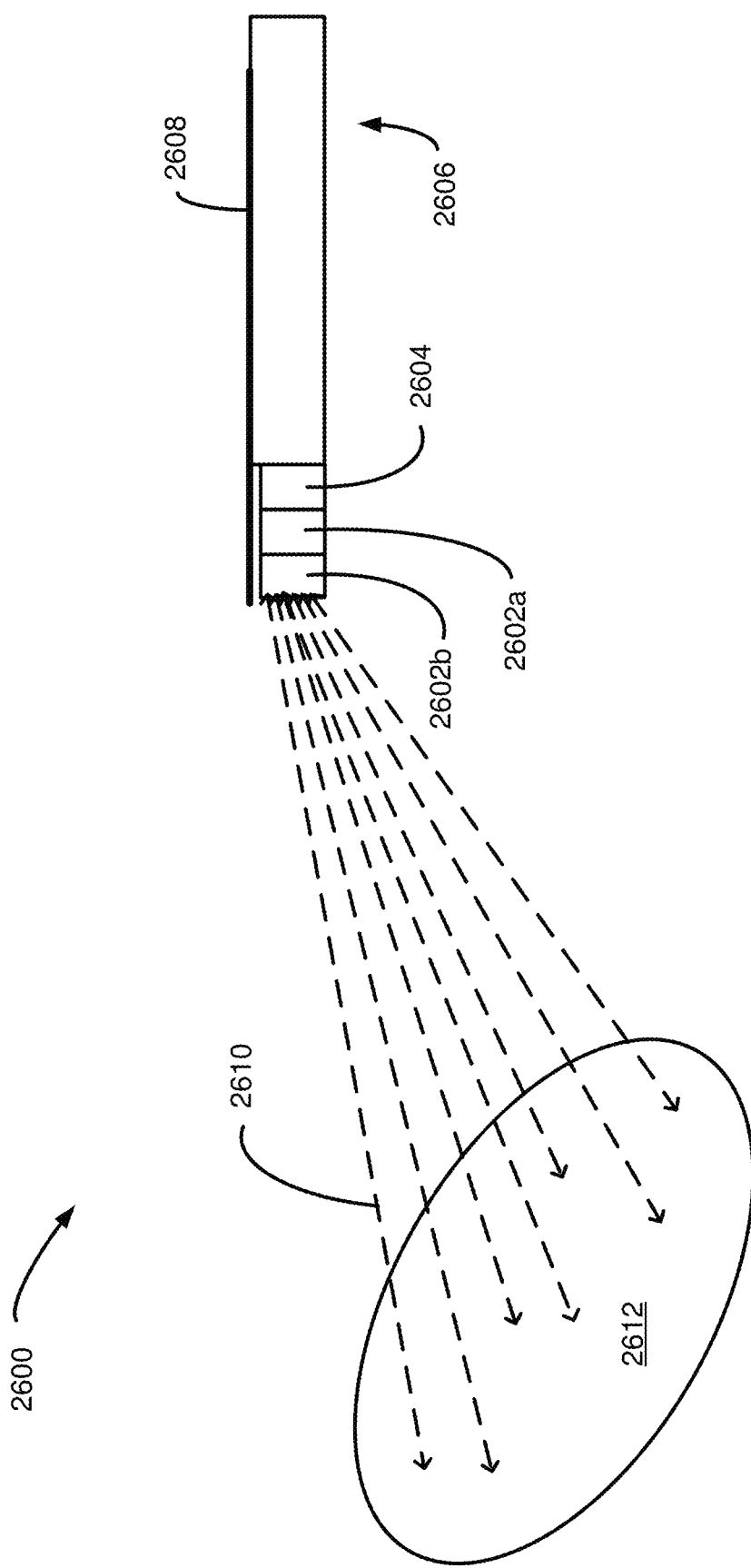
FIG. 26 illustrates an imaging system comprising a multiple cut filter for filtering wavelengths of electromagnetic radiation.

FIG. 26 is a schematic diagram of an imaging system 2600 having multiple cut filters. The system 2600 includes an endoscope 2606 or other suitable imaging device having a light source 2608 for use in a light deficient environment. The endoscope 2606 includes an image sensor 2604 and two filters 2602a, 2602b. It should be appreciated that in alternative embodiments, the system 2600 may include any number of filters, and the number of filters and the type of filters may be selected for a certain purpose e.g., for gathering imaging information of a particular body tissue, body condition, chemical process, and so forth. The filters 2602a, 2602b are configured for preventing unwanted wavelengths of light or other electromagnetic radiation from being sensed by the image sensor 2604. The filters 2602a, 2602b may be configured to filter out unwanted wavelengths from white light or other electromagnetic radiation that may be emitted by the light source 2608.

Further to the disclosure with respect to FIG. 25, the filters 2602a, 2602b may be used in an implementation where a fluorescent reagent or dye has been administered. The filters 2602a, 2602b may be configured for blocking an emitted excitation wavelength for the reagent or dye and permitting the image sensor 2604 to only read the relaxation wavelength of the reagent or dye. Further, the filters 2602a, 2602b may be used in an implementation where a fluorescent reagent or dye has not been administered. In such an implementation, the filters 2602a, 2602b may be selected to permit wavelengths corresponding to a desired spectral response to pass through and be read by the image sensor 2604.

The multiple filters 2602a, 2602b may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 2604.

In an embodiment, the filters 2602a, 2602b are customized such that electromagnetic radiation between 513 nm and 545 nm contacts the image sensor 2604. In an embodiment, the filters 2602a, 2602b are customized such that electromagnetic radiation between 565 nm and 585 nm contacts the image sensor 2604. In an embodiment, the filters 2602a, 2602b are customized such that electromagnetic radiation between 900 nm and 1000 nm contacts the image sensor 2604. In an embodiment, the filters 2602a, 2602b are customized such that electromagnetic radiation between 425 nm and 475 nm contacts the image sensor 2604. In an embodiment, the filters 2602a, 2602b are customized such that electromagnetic radiation between 520 nm and 545 nm contacts the image sensor 2604. In an embodiment, the filters 2602a, 2602b are customized such that electromagnetic radiation between 625 nm and 645 nm contacts the image sensor 2604. In an embodiment, the filters 2602a, 2602b are customized such that electromagnetic radiation between 760 nm and 795 nm contacts the image sensor 2604. In an embodiment, the filters 2602a, 2602b are customized such that electromagnetic radiation between 795 nm and 815 nm contacts the image sensor 2604. In an embodiment, the filters 2602a, 2602b are customized such that electromagnetic radiation between 370 nm and 420 nm contacts the image sensor 2604. In an embodiment, the filters 2602a, 2602b are customized such that electromagnetic radiation between 600 nm and 670 nm contacts the image sensor 2604. In an embodiment, the filters 2602a, 2602b are configured for permitting only a certain fluorescence relaxation emission to pass through the filters 2602a, 2602b and contact the image sensor 2604. In an embodiment, a first filter blocks electromagnetic radiation having a wavelength from about 770 nm to about 790 nm, and a second filter blocks electromagnetic radiation having a wavelength from about 795 nm to about 815 nm.

In an embodiment, the system 2600 includes multiple image sensors 2604 and may particularly include two image sensors for use in generating a three-dimensional image. The image sensor(s) 2604 may be color/wavelength agnostic and configured for reading any wavelength of electromagnetic radiation that is reflected off the surface 2612. In an embodiment, the image sensors 2604 are each color dependent or wavelength dependent and configured for reading electromagnetic radiation of a particular wavelength that is reflected off the surface 2612 and back to the image sensors 2604. Alternatively, the image sensor 2604 may include a single image sensor with a plurality of different pixel sensors configured for reading different wavelengths or colors of light, such as a Bayer filter color filter array. Alternatively, the image sensor 2604 may include one or more color agnostic image sensors that may be configured for reading different wavelengths of electromagnetic radiation according to a pulsing schedule such as those illustrated in FIGS. 5-7E, for example.

Figure 27A:
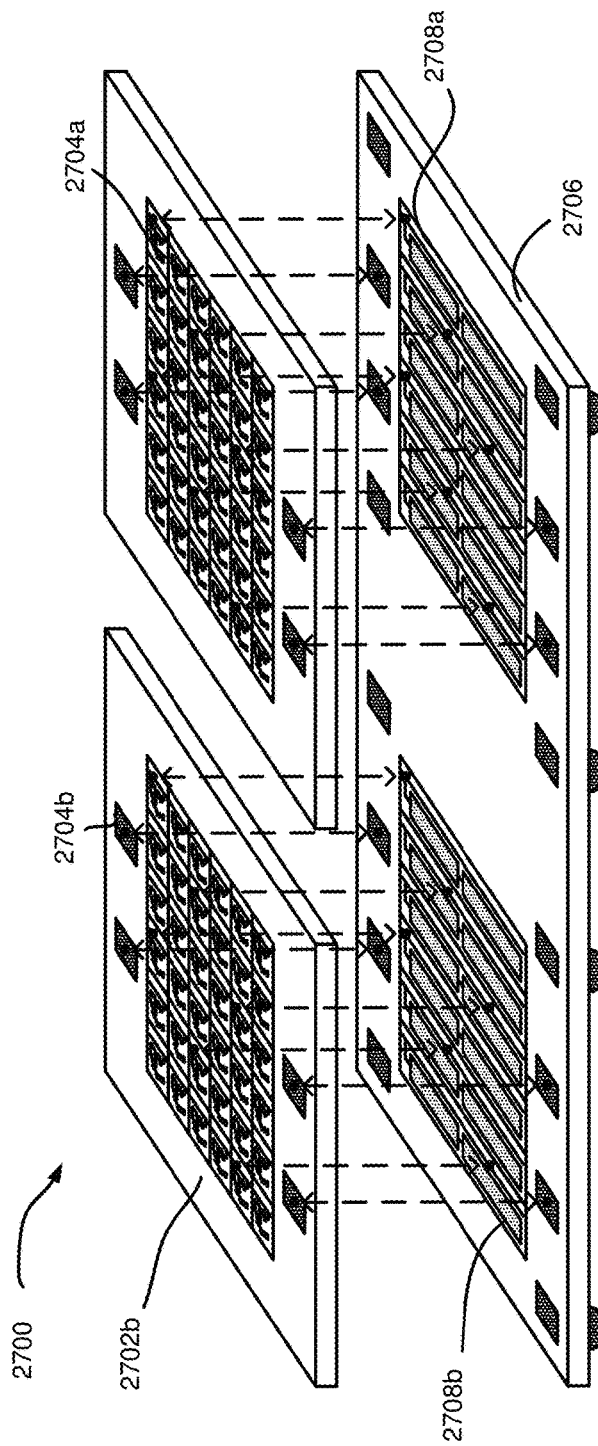
FIGS. 27A and 27B illustrate a perspective view and a side view, respectively, of an implementation of an imaging sensor having a plurality of pixel arrays for producing a three-dimensional image, wherein the plurality of pixel arrays and the image sensor are built on a plurality of substrates.
Figure 27B:
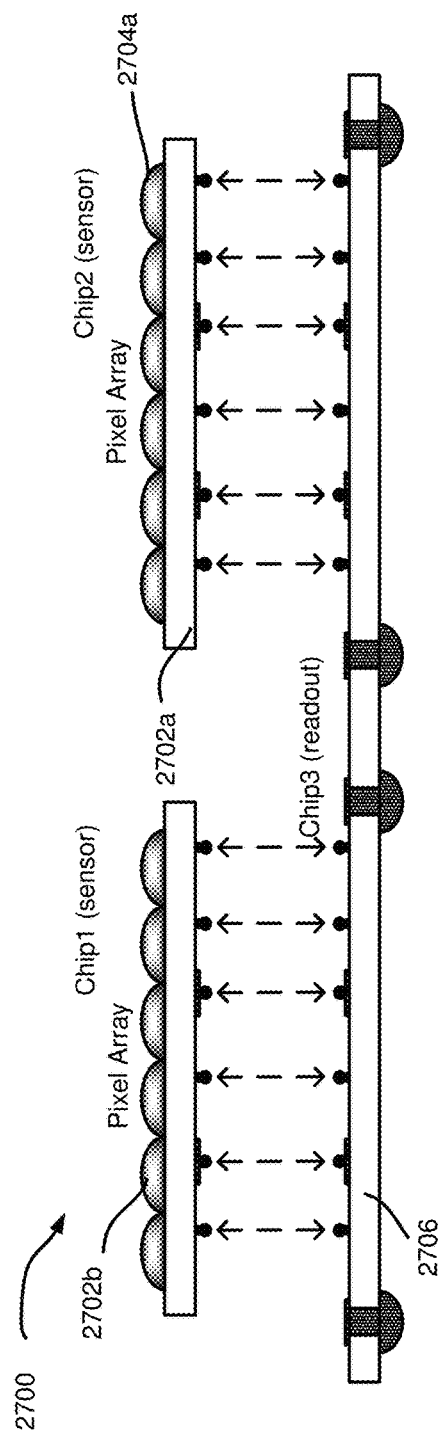

FIGS. 27A and 27B illustrate a perspective view and a side view, respectively, of an implementation of an imaging sensor 2700 having a plurality of pixel arrays for producing a three-dimensional image. The three-dimensional image sensor may be built on a plurality of substrates and may comprise the plurality of pixel arrays and other associated circuitry, wherein a plurality of pixel columns 2704a forming the first pixel array and a plurality of pixel columns 2704b forming a second pixel array are located on respective substrates 2702a and 2702b, respectively, and a plurality of circuit columns 2708a and 2708b are located on a separate substrate 2706. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

FIGS. 28A and 28B illustrate a perspective view and a side view, respectively, of an implementation of a monolithic sensor 2800 having a plurality of pixel arrays for producing a three-dimensional image in accordance with the teachings and principles of the disclosure. Such an implementation may be desirable for three-dimensional image capture, wherein the two-pixel arrays 2802 and 2804 may be offset during use. In another implementation, a first pixel array 2802 and a second pixel array 2804 may be dedicated to receiving a predetermined range of wave lengths of electromagnetic radiation, wherein the first pixel array is dedicated to a different range of wavelength electromagnetic radiation than the second pixel array.

Figure 29A:
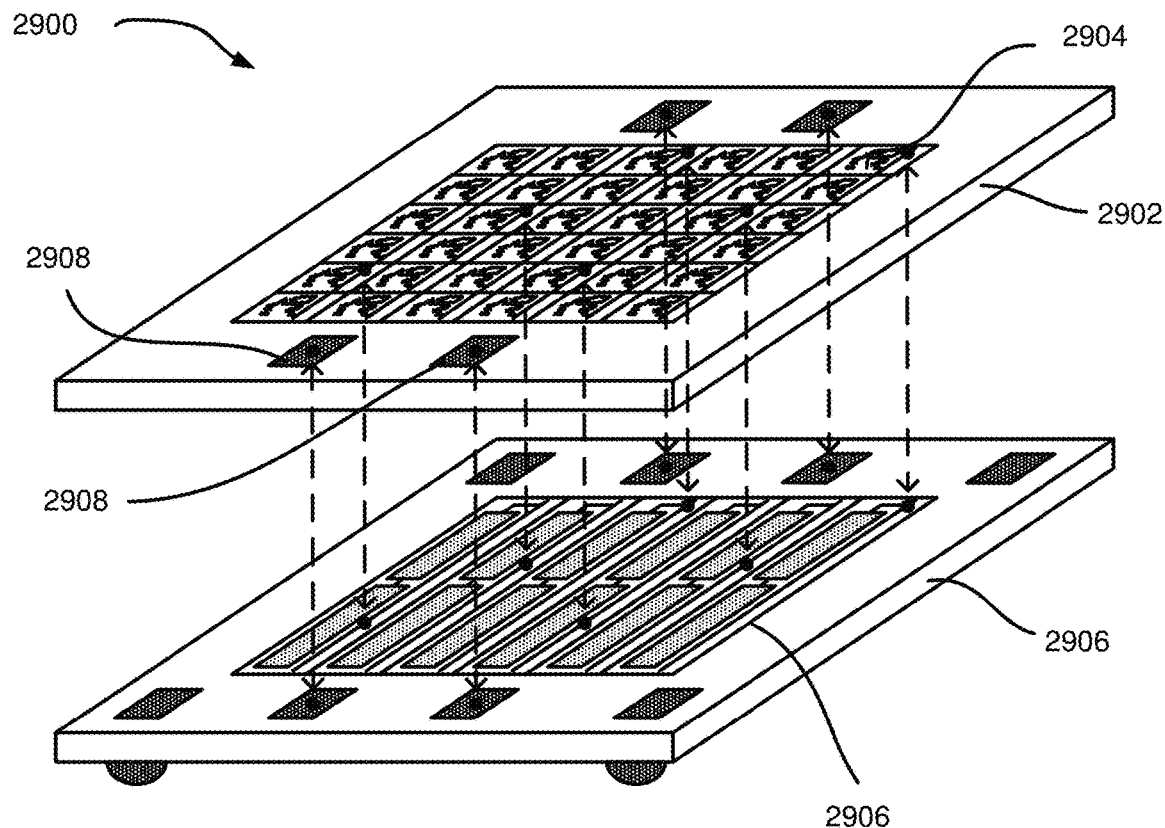
FIGS. 29A and 29B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 29B:
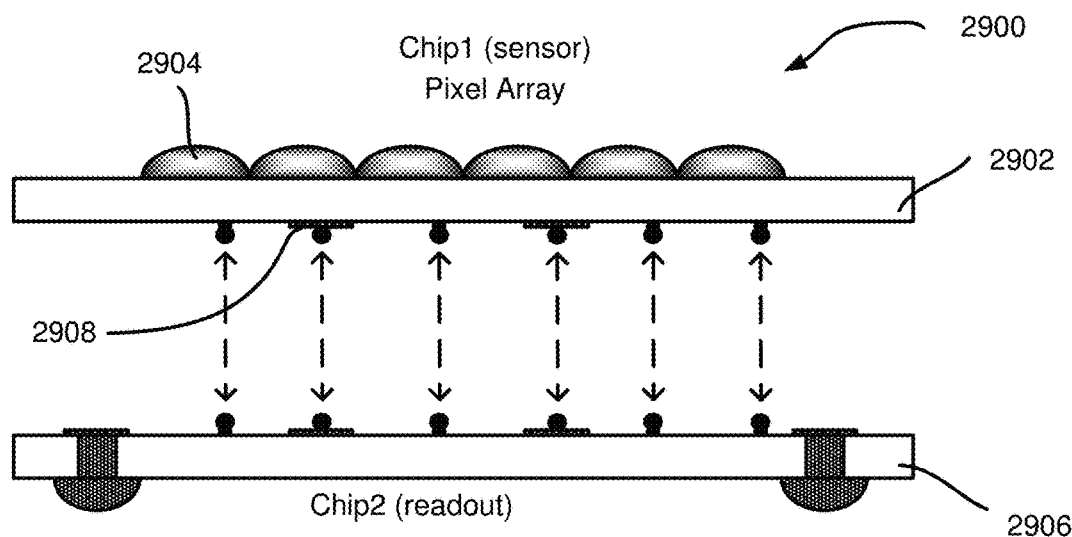

FIGS. 29A and 29B illustrate a perspective view and a side view, respectively, of an implementation of an imaging sensor 2900 built on a plurality of substrates. As illustrated, a plurality of pixel columns 2904 forming the pixel array are located on the first substrate 2902 and a plurality of circuit columns 2908 are located on a second substrate 2906. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 2902 of the 2902 substrates/chips may be processed using an image CMOS process. The first substrate/chip 2902 may be comprised either of a pixel array exclusively or a pixel array surrounded by limited circuitry. The second or subsequent substrate/chip 2906 may be processed using any process and does not have to be from an image CMOS process. The second substrate/chip 2906 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 2902 may be stacked with the second or subsequent substrate/chip 2906 using any three-dimensional technique. The second substrate/chip 2906 may support most, or a majority, of the circuitry that would have otherwise been implemented in the first image CMOS chip 2902 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

Examples

The following examples pertain to preferred features of further embodiments:

Example 1 is a system. The system includes an emitter for emitting pulses of electromagnetic radiation and an image sensor comprising a pixel array for sensing reflected electromagnetic radiation. The system includes a plurality of bidirectional data pads in the image sensor for outputting image data and receiving configuration data. The system includes a controller in electronic communication with the image sensor and the emitter. The system is such that at least a portion of the pulses of electromagnetic radiation emitted by the emitter comprises one or more of: electromagnetic radiation having a wavelength from about 770 nm to about 790 nm.

Example 2 is a system as in Example 1, further comprising: an oscillator disposed in the controller; and a frequency detector in electronic communication with controller to control a clock frequency of the image sensor in response to signals from the controller that correspond to the frequency of the oscillator.

Example 3 is a system as in any of Examples 1-2, wherein electronic communication through each of the plurality of bidirectional pads is performed in defined phases comprising: a rolling readout phase during which the image data is output from the image sensor through the plurality of bidirectional pads to the controller; a service line phase during which non-image data is output from the image sensor through the plurality of bidirectional pads to the controller; and a configuration phase during which image sensor configuration data is received by the image sensor from the controller through the plurality of bidirectional pads; wherein image sensor data output lines are reversed during the configuration phase; and wherein a clock data recovery circuit is unlocked from an oscillator disposed in the controller when the image sensor data output lines are reversed.

Example 4 is a system as in any of Examples 1-3, wherein clock signal data is transmitted during the service line phase and the configuration phase and is not transmitted during the rolling readout phase.

Example 5 is a system as in any of Examples 1-4, wherein the image sensor does not comprise a dedicated input synchronization clock pad such that a total number of bidirectional pads in the image sensor is reduced.

Example 6 is a system as in any of Examples 1-5, further comprising an oscillator disposed in the controller for providing a reference clock frequency to synchronize incoming sensor data.

Example 7 is a system as in any of Examples 1-6, further comprising at least one transition within pixel serial data created by the pixel array of the image sensor, wherein the pixel serial data is replaced in the pixel array according to synchronization determined by clock signal data.

Example 8 is a system as in any of Examples 1-7, further comprising: a phase lock loop (PLL) comprising PLL image sensor blocks and PLL controller blocks; data lines electrically connecting the PLL image sensor blocks and the PLL controller blocks; and configuration lines electrically connecting the PLL image sensor blocks and the PLL controller blocks; wherein an oscillator disposed in the controller and a data recovery circuit are used to lock on to incoming data received by the controller from the image sensor.

Example 9 is a system as in any of Examples 1-8, wherein the image sensor is configured to generate a plurality of exposure frames, wherein each of the plurality of exposure frames corresponds to a pulse of electromagnetic radiation emitted by the emitter.

Example 10 is a system as in any of Examples 1-9, wherein the pixel array of the image sensor senses reflected electromagnetic radiation to generate the plurality of exposure frames during a readout period of the pixel array, wherein the readout period is a duration of time when active pixels in the pixel array are read.

Example 11 is a system as in any of Examples 1-10, wherein at least a portion of the plurality of exposure frames are combined to form an image frame.

Example 12 is a system as in any of Examples 1-11, further comprising: a voltage controlled oscillator; a phase lock loop based on a charge pump for driving the voltage controlled oscillator; and a phase lock loop based on a digital-to-analog converter for driving the voltage controlled oscillator.

Example 13 is a system as in any of Examples 1-12, wherein the emitter is configured to emit, during a pulse duration, a plurality of sub-pulses of electromagnetic radiation having a sub-duration shorter than the pulse duration.

Example 14 is a system as in any of Examples 1-13, wherein one or more of the pulses of electromagnetic radiation emitted by the emitter comprise electromagnetic radiation emitted at two or more wavelengths simultaneously as a single pulse or a single sub-pulse.

Example 15 is a system as in any of Examples 1-14, wherein at least a portion of the pulses of electromagnetic radiation emitted by the emitter is a fluorescence emission for exciting a fluorescent reagent, wherein the fluorescence emission results in a fluorescence exposure frame created by the image sensor, and wherein the controller is configured to provide the fluorescence exposure frame to a corresponding system that determines a location of a critical tissue structure within a scene based on the fluorescence exposure frame.

Example 16 is a system as in any of Examples 1-15, wherein the fluorescence emission comprises the electromagnetic radiation having the wavelength from about 770 nm to about 790 nm and the electromagnetic radiation having the wavelength from about 795 nm to about 815 nm.

Example 17 is a system as in any of Examples 1-16, wherein the controller is further configured to: receive the location of the critical tissue structure from the corresponding system; generate an overlay frame comprising the location of the critical tissue structure; and combine the overlay frame with a color image frame depicting the scene to indicate the location of the critical tissue structure within the scene.

Example 18 is a system as in any of Examples 1-17, wherein the critical structure comprises one or more of a nerve, a ureter, a blood vessel, an artery, a blood flow, or a tumor.

Example 19 is a system as in any of Examples 1-18, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

Example 20 is a system as in any of Examples 1-19, wherein two or more pulses of electromagnetic radiation emitted by the emitter result in two or more instances of reflected electromagnetic radiation that are sensed by the pixel array to generate two or more exposure frames that are combined to form an image frame.

Example 21 is a system as in any of Examples 1-20, wherein the image sensor comprises a first image sensor and a second image sensor such that the image sensor can generate a three-dimensional image.

Example 22 is a system as in any of Examples 1-21, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 23 is a system as in any of Examples 1-22, wherein the pulses of electromagnetic radiation are emitted in a pattern of varying wavelengths of electromagnetic radiation, and wherein the emitter repeats the pattern of varying wavelengths of electromagnetic radiation Example 24 is a system as in any of Examples 1-23, wherein at least a portion of the pulses of electromagnetic radiation emitted by the emitter comprises a fluorescence emission for exciting a fluorescent reagent, wherein the fluorescence emission comprises the electromagnetic radiation having the wavelength from about 770 nm to about 790 nm and the electromagnetic radiation having the wavelength from about 795 nm to about 815 nm.

Example 25 is a system as in any of Examples 1-24, wherein at least a portion of the pulses of electromagnetic radiation emitted by the emitter is an excitation wavelength for fluorescing a reagent, and wherein at least a portion of the reflected electromagnetic radiation sensed by the pixel array is a relaxation wavelength of the reagent.

Example 26 is a system as in any of Examples 1-25, wherein at least a portion of the pulses of electromagnetic radiation comprise a red wavelength, a green wavelength, a blue wavelength, and a fluorescence wavelength such that reflected electromagnetic radiation sensed by the pixel array corresponding to each of the red wavelength, the green wavelength, the blue wavelength, and the fluorescence wavelength can be processed to generate a Red-Green-Blue (RGB) image comprising an overlay of fluorescence imaging data, wherein the fluorescence wavelength of electromagnetic radiation comprises the electromagnetic radiation having the wavelength from about 770 nm to about 790 nm and the electromagnetic radiation having the wavelength from about 795 nm to about 815 nm.

Example 27 is a system as in any of Examples 1-26, further comprising a filter that filters electromagnetic radiation having a wavelength from about 770 nm to about 790 nm.

Example 28 is a system as in any of Examples 1-27, further comprising a filter that filters electromagnetic radiation having a wavelength from about 795 nm to about 815 nm.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
   an emitter comprising a plurality of electromagnetic sources configured to emit a plurality of pulses of electromagnetic radiation;
   an image sensor comprising a pixel array that detects electromagnetic radiation and reads out a plurality of exposure frames according to a sensor cycle that comprises a plurality of variable blanking periods and a plurality of readout periods;
   a plurality of bidirectional data pads on the image sensor for outputting image data and receiving configuration data; and
   a controller in electronic communication with the image sensor and the emitter;
   wherein the configuration data received by the image sensor comprises timing data for reading out the plurality of exposure frames according to the sensor cycle;
   wherein a duration of each of the plurality of variable blanking periods of the image sensor is adjustable such that the sensor cycle comprises two or more blanking periods having a different duration;
   wherein at least one of the plurality of electromagnetic sources of the emitter is a fluorescence source tuned to pulse electromagnetic radiation within a waveband from about 770 nm to about 795 nm; and
   wherein each of the plurality of variable blanking periods is adjustable based on an amount of energy emitted by the emitter during a pulse duration.

2. The system of claim 1, further comprising:
   an oscillator disposed in the controller; and
   a frequency detector in electronic communication with the controller to control a clock frequency of the image sensor in response to signals from the controller that correspond to the frequency of the oscillator.

3. The system of claim 1, wherein electronic communication through each of the plurality of bidirectional pads is performed in defined phases comprising:
   a rolling readout phase during which image data is output from the image sensor through the plurality of bidirectional pads to the controller;
   a service line phase during which non-image data is output from the image sensor through the plurality of bidirectional pads to the controller; and
   a configuration phase during which image sensor configuration data is received by the image sensor from the controller through the plurality of bidirectional pads;
   wherein image sensor data output lines are reversed during the configuration phase; and
   wherein a clock data recovery circuit is unlocked from an oscillator disposed in the controller when the image sensor data output lines are reversed.

4. The system of claim 3, wherein clock signal data is transmitted during the service line phase and the configuration phase and is not transmitted during the rolling readout phase.

5. The system of claim 1, wherein the image sensor does not comprise a dedicated input synchronization clock pad such that a total number of data pads in the image sensor is reduced.

6. The system of claim 1, further comprising an oscillator disposed in the controller for providing a reference clock frequency to synchronize incoming data received from the image sensor.

7. The system of claim 1, further comprising at least one transition within pixel serial data created by the pixel array of the image sensor, wherein the pixel serial data is replaced in the pixel array according to synchronization determined by clock signal data.

8. The system of claim 1, further comprising:
   a phase lock loop (PLL) comprising PLL image sensor blocks and PLL controller blocks;
   data lines electrically connecting the PLL image sensor blocks and the PLL controller blocks; and
   configuration lines electrically connecting the PLL image sensor blocks and the PLL controller blocks;
   wherein an oscillator disposed in the controller and a data recovery circuit are used to lock on to incoming data received by the controller from the image sensor.

9. The system of claim 1, wherein the controller instructs the emitter to emit the plurality of pulses of electromagnetic radiation according to a variable pulse cycle; and wherein the variable pulse cycle of the emitter is synchronized with the sensor cycle of the image sensor such that the pixel array detects the electromagnetic radiation and reads out data for generating an exposure frame in response to each pulse of electromagnetic radiation emitted by the emitter.

10. The system of claim 1, wherein the image sensor reads out data during the plurality of readout periods to output the plurality of exposure frames;
wherein the pixel array accumulates electromagnetic radiation during at least a portion of the plurality of variable blanking periods; and
wherein the controller synchronizes operations of the emitter and the image sensor such that the emitter cycles on at least one of the plurality of electromagnetic sources during at least the portion of the plurality of blanking periods; and
wherein the controller synchronizes operations of the emitter and the image sensor such that the emitter cycles off each of the plurality of electromagnetic sources during the plurality of variable blanking periods of the sensor cycle.

11. The system of claim 1, wherein two more of the plurality of exposure frames are combined to generate an overlay frame comprising color imaging data and fluorescence imaging data.

12. The system of claim 1, further comprising:
a voltage-controlled oscillator;
a phase lock loop based on a charge pump for driving the voltage-controlled oscillator; and
a phase lock loop based on a digital-to-analog converter for driving the voltage-controlled oscillator.

13. The system of claim 1, wherein the pixel array detects the electromagnetic radiation and outputs data for one exposure frame subsequent to one pulse duration.

14. The system of claim 1, wherein the controller instructs the emitter to actuate the plurality of electromagnetic sources according to a variable pulse cycle comprising a plurality of independent pulse durations, and wherein the controller instructs the emitter to pulse two or more wavelengths simultaneously or independently during at least one pulse duration of the plurality of independent pulse durations.

15. The system of claim 1, wherein the plurality of electromagnetic sources of the emitter comprises:
a visible source tuned to pulse electromagnetic radiation within a visible waveband of the electromagnetic spectrum; and
the fluorescence source;
wherein the pixel array detects the electromagnetic radiation and outputs data for generating a fluorescence exposure frame in response to the fluorescence source pulsing the electromagnetic radiation within the near-infrared waveband.

16. The system of claim 15, wherein the fluorescence source is finely tuned to emit electromagnetic radiation only within the waveband from about 770 nm to about 795 nm.

17. The system of claim 15, wherein the controller is configured to:
provide the fluorescence exposure frame to a corresponding system that determines one or more of an identity or a location of a tissue structure within a scene based on the data for the fluorescence exposure frame;
receive one or more of the identity or the location of the tissue structure from the corresponding system;
generate an overlay frame comprising an overlay highlighting the location of the tissue structure overlaid on a color image frame depicting the scene to indicate the location of the tissue structure within the scene.

18. The system of claim 17, wherein the tissue structure comprises one or more of a nerve, a ureter, a blood vessel, an artery, a blood flow, or a tumor.

19. The system of claim 1, wherein each of the plurality of variable blanking periods of the sensor cycle corresponds to a time between a readout of a last row of active pixels in the pixel array and a beginning of a next subsequent readout of active pixels in the pixel array; and
wherein the duration of each of the plurality of variable blanking periods is adjustable to ensure sufficient exposure in a corresponding exposure frame read out by the image sensor.

20. The system of claim 1, wherein the two or more blanking periods having the different duration comprises a first blanking period having a first duration and a second blanking period having a second duration;
wherein the emitter pulses a first emission during the first blanking period;
wherein the emitter pulses a second emission during the second blanking period; and
wherein the first duration and the second duration are determined at least in part based on relative intensities of the first emission and the second emission.

21. The system of claim 1, wherein the image sensor comprises a first image sensor and a second image; and
wherein simultaneous outputs from the first image sensor and the second image sensor are utilized to generate a three-dimensional image.

22. The system of claim 1, wherein the emitter pulses the plurality of pulses of electromagnetic radiation according to a variable pulse cycle, and wherein the emitter repeats the variable pulse cycle at a speed sufficient for generating a video stream comprising color imaging data and fluorescence imaging data.

23. The system of claim 1, wherein the emitter pulses the plurality of pulses of electromagnetic radiation according to a variable pulse cycle comprising two or more different wavelengths of electromagnetic radiation:
wherein the controller adjusts the variable pulse cycle based on user input; and
wherein the variable pulse cycle alternates between the two or more different wavelengths of electromagnetic radiation.

24. The system of claim 1, wherein the fluorescence source is tuned to emit a fluorescence excitation emission that excites a fluorescent reagent; and
wherein the image sensor detects the electromagnetic radiation and reads out a fluorescence exposure frame in response to the emitter pulsing the fluorescence excitation emission; and
wherein the fluorescence exposure frame comprises data for identifying a location of the fluorescent reagent within a scene.

25. The system of claim 1, wherein at least a portion of the plurality of pulses of electromagnetic radiation emitted by the emitter is an excitation wavelength for fluorescing a reagent, and wherein the pixel array detects a relaxation wavelength of the reagent in response to the emitter pulsing the excitation wavelength.

26. The system of claim 1, wherein the controller instructs the emitter to cycle the plurality of electromagnetic sources according to a variable pulse cycle, wherein the variable pulse cycle comprises:

a visible pulse comprising white light; and a fluorescence pulse emitted by the fluorescence source, wherein the fluorescence pulse comprises electromagnetic radiation within the waveband from about 770 nm to about 795 nm;

wherein the pixel array detects the electromagnetic radiation and outputs a color exposure frame corresponding with the visible pulse and a fluorescence exposure frame corresponding with the fluorescence pulse; and wherein the color exposure frame and the fluorescence exposure frames are processed to generate a Red-Green-Blue (RGB) image comprising an overlay highlighting a location of a target tissue structure within a scene.

27. The system of claim 1, further comprising a filter that filters electromagnetic radiation having a wavelength from about 770 nm to about 795 nm.

* * * * *